United States Patent
Kamei et al.

Patent Number: 6,114,522
Date of Patent: Sep. 5, 2000

[54] PROCESS OF PRODUCTION OF 4-SUBSTITUTED-3-HALOGENO-1,4-BENZOXAZEPINE DERIVATIVE AND SALTS THEREOF

[75] Inventors: Kastuhide Kamei; Noriko Maeda, both of Takatsuki; Toshio Tatsuoka, Nishinomiya, all of Japan

[73] Assignee: Suntory Limited, Osaka, Japan

[21] Appl. No.: 09/254,719

[22] PCT Filed: Jul. 14, 1998

[86] PCT No.: PCT/JP98/03153

§ 371 Date: Nov. 24, 1999

§ 102(e) Date: Nov. 24, 1999

[87] PCT Pub. No.: WO99/03847

PCT Pub. Date: Jan. 28, 1999

[30] Foreign Application Priority Data

Jul. 14, 1997 [JP] Japan ........................ 9-188670

[51] Int. Cl.⁷ .................. C07D 267/14; C07D 413/12; C07D 413/14
[52] U.S. Cl. .......................... 540/490; 540/487
[58] Field of Search ............................. 540/490

[56] References Cited

FOREIGN PATENT DOCUMENTS 0 755 930 A1  1/1997  European Pat. Off. .

OTHER PUBLICATIONS

Lee et al, "The Reaction of Vinyl Phosphates and Iodotrimethylsilane: Synthesis of Vinyl Iodides from Ketones", *Tetrahedron Letters*, vol. 34, No. 15, pp. 2433–2436, Apr. 9, 1993.

*Primary Examiner*—Fiona T. Powers
*Attorney, Agent, or Firm*—Burns, Doane, Swecker & Mathis, L.L.P.

[57] ABSTRACT

A process for producing 4-substituted-3-halogeno-1,4-benzoxazepin derivative or the salt thereof comprising:
deprotonizing a benzoxazepine derivative having the formula (II):

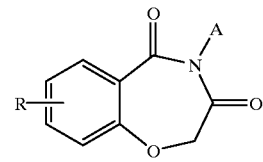

with a base; and then,
reacting the deprotonized product with a phosphate halide to produce an intermediate having the formula (IV):

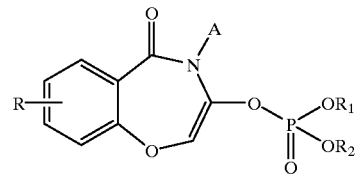

and then,
reacting the resultant intermediate (IV) with a reagent selected from (i) a complex of a phosphine with chlorine or bromine, (ii) a phosphine and a chlorine gas or liquid bromine, (iii) a phosphine and tetrachloromethane or tetrabromomethane, or (iv) a halogenated phosphite ester to produce a 4-substituted-3-halogeno-1,4-benzoxazepine derivative having the formula (I)

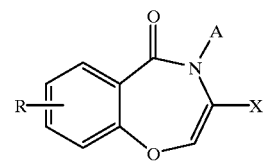

wherein
X indicates a chlorine atom or a bromine atom, or its salt.

5 Claims, No Drawings

PROCESS OF PRODUCTION OF 4-SUBSTITUTED-3-HALOGENO-1,4-BENZOXAZEPINE DERIVATIVE AND SALTS THEREOF

This application is a 371 of PCT/JP98/03153 filed Jul. 14, 1998.

TECHNICAL FIELD

The present invention relates to process for the production of a 4-substituted-3-halogeno-1,4-benzoxazepine derivative and the salts thereof, which are useful as a pharmaceutical or as a starting material or intermediate for the synthesis thereof.

BACKGROUND ART

A 4-substituted-3-halogeno-1,4-benzoxazepine derivative is an important compound usable as a pharmaceutical for psychoneurotic disorders such as anxiety neurosis, phobias, obsessive-compulsive disorders, schizophrenia, post-cardiac trauma stress disorders, depression disorders, and psychosomatic disorders, disorders such as eating disorders, menopausal disorders, infantile autism and also emesis or disorders involving the cerebral circulatory system accompanying cerebral infarction and cerebral hemorrhaging or as a synthetic starting material or an intermediate of pharmaceuticals etc. However, industrial processes for production thereof which have been fully satisfactory in terms of the operability and yield, are not known in the art.

A process for synthesis of a 4-substituted-3-halogeno-1,4-benzoxazepine derivative is disclosed in, for example, International Publication WO96-24594. That is, this process comprises reacting a benzoxazepine derivative with an acid chloride such as phosphorus oxychloride ($POCl_3$), thionyl chloride ($SOCl_2$), while adding acid such as hydrochloric acid or a base such as N,N-diethylaniline, if necessary. However, in this process, since a large amount of acid chloride is used, there is the accompanying risk of the generation of hydrochloric acid gas and a sudden rise in temperature and the generation of bumping, etc. in the neutralization reaction for treatment and decomposition of the excessive acid chloride and, therefore, there was the industrial difficulty. Further, in terms of the yield as well, the yield was 30 to 60%—which cannot be necessarily said to be good. Further, there was the problem that the benzoxazepine derivative starting material would remain in the reaction solution in considerable amounts and it was difficult to separate the starting material compound and the target compound.

In this way, no process has been known which has been fully satisfactory for the industrial production of a 4-substituted-3-halogeno-1,4-benzoxazepine derivative. Therefore, a new process for production of a 4-substituted-3-halogeno-1,4-benzoxazepine derivative is necessary to be developed.

SUMMARY OF THE INVENTION

Accordingly, an object of the present invention is to provide a new process for production of a 4-substituted-3-halogeno-1,4-benzoxazepine derivative and the salts thereof which are easy to operate and which are industrially satisfactory and which are good yield.

Another object of the present invention is to provide an industrially satisfactory process for production of a benzoxazepine derivative and the salts thereof using the above process.

In accordance with the present invention, there is provided a 4-substituted-3-halogeno-1,4-benzoxazepine derivative having the formula (I):

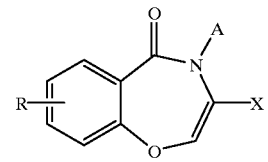

(I)

wherein, R indicates a hydrogen atom, halogen atom, $C_1$ to $C_4$ lower alkyl group, $C_1$ to $C_4$ lower alkoxy group, or hydroxy group, preferably a hydrogen atom or halogen atom, and A indicates a $C_2$ to $C_5$ halogenoalkyl group or a group having the formula (III):

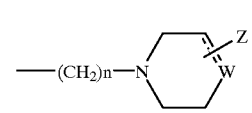

(III)

wherein, n is an integer of 2 to 5, the dotted line indicates the presence or absence of a bond, W indicates a carbon atom, methine, methylene, or nitrogen atom, where when W is a nitrogen atom, Z bonds with W and the dotted line indicates the absence of a bond, and Z indicates an aromatic hydrocarbon group which may be substituted, or a heterocyclic group which may be substituted, preferably a $C_2$–$C_5$ halogenoalkyl group or a group having the formula (XXVI) or (XXVII):

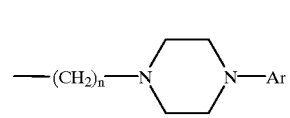

(XXVI)

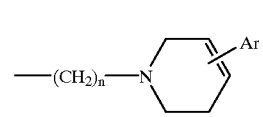

(XXVII)

wherein n is an integer of 2 to 5, Ar is a phenyl group, 2-pyridyl group or 2-pyrimidinyl group, X indicates a chlorine atom or bromine atom, preferably a chlorine atom, can be produced by deprotonizing, using a base, a benzoxazepine derivative having the formula (II):

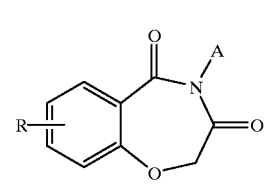

(II)

wherein, R and A are the same as defined above, then reacting the deprotonized product with a phosphate halide to produce an intermediate having the formula (IV):

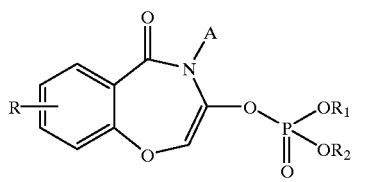

wherein, R and A are as defined above, and $R_1$ and $R_2$, independently, indicate, a $C_1$ to $C_2$ lower alkyl group or phenyl group or $R_1$ and $R_2$ together indicate an ethylene group (—$CH_2CH_2$—), then reacting this intermediate (IV) with a reagent selected from (i) a complex of a tri($C_1$ to $C_4$) alkylphosphine, triarylphosphine, or phenyldi($C_1$ to $C_4$) alkylphosphine with chlorine or bromine, (ii) a tri($C_1$ to $C_4$) alkylphosphine, triarylphosphine, or phenyldi($C_1$ to $C_4$) alkylphosphine and chlorine gas or liquid bromine, (iii) tri($C_1$ to $C_4$) alkylphosphine, triarylphosphine, or phenyldi($C_1$ to $C_4$) alkylphosphine and tetrachloromethane or tetrabromomethane, or (iv) a halogenated phosphite ester to produce the 4-substituted-3-halogeno-1,4-benzoxazepine derivative (I).

BEST MODE FOR CARRYING OUT THE INVENTION

The present inventors engaged in intensive research with the aim of development of an industrial process of production of a 4-substituted-3-halogeno-1,4-benzoxazepine derivative in view of the above situation and, as a result, found that, by using a starting material having the above formula (II) to derive a phosphate ester having the formula (IV) and then react this intermediate (IV) with a reagent selected from (i) a complex of a tri($C_1$ to $C_4$) alkylphosphine (for example, $Me_3P$, $Et_3P$, $Pr_3P$, $BU_3P$), triarylphosphine (preferably, triphenylphosphine), or phenyldi($C_1$ to $C_4$) alkylphosphine (preferably, $PhPMe_2$, $PhPEt_2$) with chlorine or bromine, (ii) a tri($C_1$ to $C_4$) alkylphosphine, triarylphosphine, or phenyldi($C_1$ to $C_4$) alkylphosphine and chlorine gas or liquid bromine, (iii) a tri($C_1$ to $C_4$) alkylphosphine, triarylphosphine, or phenyldi($C_1$ to $C_4$) alkylphosphine and tetrachloromethane or tetrabromomethane, or (iv) a halogenated (preferably, chlorinated or brominated) phosphite ester, it was possible to obtain a 4-substituted-3-halogeno-1,4-benzoxazepine derivative easily and with a good yield.

The starting material, that is, the compound having the above formula (II), can be prepared by the process disclosed in International Publication WO96-24594. The compound having the above formula (IV) can be obtained by deprotonizing the compound having the above formula (II) with a base such as potassium tert-butoxide, potassium bis(trimethylsilyl)amide, sodium bis(trimethylsilyl) amide, sodium hydride, triethylamine, lithium bis(trimethylsilyl) amine or sodium amide, then treating the resultant product with a phosphate chloride compound such as diethyl chlorophosphate, diphenyl chlorophosphate, or 2-chloro-1,3,2-dioxaphospholane-2-oxide.

The desired 4-substituted-3-halogeno-1,4-benzoxazepine derivative having the formula (I) can be produced by the method of combining the compound thus obtained having the above formula (IV) with a commercially available triphenylphosphine-chlorine complex, triphenylphosphine-bromine complex, or triphenylphosphine and tetrahalogenomethane (for example, $CCl_4$).

Due to the development of the process according to the present invention, it is possible to avoid the occurrence of sudden rises in temperature or bumping accompanying the neutralization and decomposition of the reagents and improve the separation and yield compared with the conventional process disclosed in the International Publication WO96-24594. Further, the problem of separation of the starting material compound and the target compound is also solved and industrial production becomes easier. A useful new process of production for the 4-substituted-3-halogeno-1,4-benzoxazepine derivative having the above formula (I) has therefore been developed. Further, by using this process, it is also possible to obtain industrially useful benzoxazepine derivatives and their salts in accordance with the process described in the International Publication WO96-24594.

I) Process of Production of Intermediate having Above Formula (IV)

The phosphate halide usable in the process of production of the intermediate having the above formula (IV) is preferably dimethyl chlorophosphate, diethyl chlorophosphate, diphenyl chlorophosphate, 2-chloro-1,3,2-dioxaphospholane-2-oxide, more preferably diethyl chlorophosphate, diphenyl chlorophbsphate, or 2-chloro-1,3,2-dioxaphospholane-2-oxide, most preferably diethyl chlorophosphate. These phosphate halides are used in amounts of preferably 1 to 3 equivalents, more preferably 1 to 1.2 equivalents, of the compound having the above formula (II).

The base which may be used in the reaction is preferably sodium hydride, sodium bis(trimethylsilyl) amide, potassium bis(trimethylsilyl)amide, lithium bis(trimethylsilyl) amide, sodium amide, or lithium diisopropylamide, more particularly sodium bis(trimethylsilyl)amide, potassium bis (trimethylsilyl)amide, lithium bis(trimethylsilyl)amide, or lithium diisopropylamide, most preferably sodium bis (trimethylsilyl)amide or potassium bis(trimethylsilyl)amide. These bases may be used in amounts of preferably 1 to 2 equivalents, more preferably 1 to 1.2 equivalents, of the compound having the above formula (II).

The reaction temperature of the reaction is not particularly limited, but preferably it is −100° C. to room temperature, more preferably −78° C. to 0° C. Further, the reaction is performed in the presence of an organic solvent. As the organic solvent, preferably tetrahydrofuran, diethyl ether, or ethylene glycol diethyl ether, more preferably tetrahydrofuran or diethyl ether, may be mentioned.

II) Process for Production of Compound having Above Formula (I) From Intermediate having Formula (IV)

The reaction product used for the process of production of the 4-substituted-3-chloro-1,4-benzoxazepine derivative where X=Cl in the compounds having the above formula (I) is preferably a triphenylphosphine-chlorine complex, chlorine in the copresence of triphenylphosphine, carbon tetrachloride in the copresence of triphenylphosphine, diethyl chlorophosphite, or phosphorus oxychloride, more preferably a triphenylphosphine-chlorine complex, chlorine in the copresence of triphenylphosphine, carbon tetrachloride in the copresence of triphenylphosphine, or diethyl chorophosphite, most preferably a triphenylphosphine-chlorine complex.

The reaction product used for the process of production of the 4-substituted-3-bromo-1,4-benzoxazepine derivative where X=Br in the compounds having the above formula (I) is preferably a triphenylphosphine-bromine complex, bromine in the copresence of triphenylphosphine, or carbon tetrabromide in the copresence of triphenylphosphine, more preferably a triphenylphosphine-bromine complex or carbon tetrabromide in the copresence of triphenylphosphine, most preferably a triphenylphosphine-bromine complex.

These reagents may be used in amounts of preferably 1 to 10 equivalents, more preferably 1 to 5 equivalents, most preferably 1 to 2 equivalents of the compound having the above formula (IV).

The reaction temperature of the reaction is not particularly limited, but preferably it is 0° C. to 80° C., more preferably room temperature to 80° C. Further, the reaction is normally performed in the presence of an organic solvent. As the organic solvent used in the reaction, preferably tetrahydrofuran, diethyl ether, ethylene glycol diethyl ether, acetonitrile, methylene chloride, 1,2-dichloroethane, hexane, or dimethyl formamide, more preferably tetrahydrofuran, diethyl ether, acetonitrile, methylene chloride, or 1,2-dichloroethane may be mentioned.

III) Process of Production of Benzoxazepine Derivative (Ib) With A of Group having Formula (III) in Compounds having Formula (I) From Compound (Ib) With A of Halogenoalkyl in Compounds of Formula (I)

The compound having the formula (Ib) may be synthesized by condensation by an ordinary method of the intermediate compound having the formula (Ia)

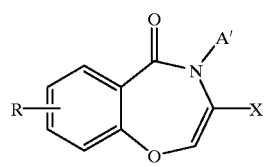
(Ia)

wherein, A' indicates a halogenoalkyl, and R and X are as the same as defined above

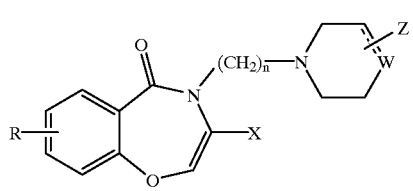
(Ib)

wherein, R and X are as defined above, n is an integer of 2 to 5, the dotted line indicates the presence or absence of a bond, W indicates C, CH, or CH$_2$ or N, where, when W is a nitrogen atom, Z bonds with W and the dotted line indicates the absence of a bond, and Z indicates a substitutable aromatic hydrocarbon cyclic group or substitutable heterocyclic group with an intermediate compound of the formula (IX):

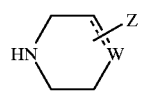
(IX)

wherein W and Z are as defined above.

Further, in the intermediate compound having the formula (Ia) provided in accordance with the present invention, as preferable examples of the halogenoalkyl group having A' in the formula, chloropentyl, bromopentyl, iodopentyl, chlorobutyl, bromobutyl, iodobutyl, chloropropyl, bromopropyl, and iodopropyl may be mentioned. In particular, chlorobutyl, bromobutyl, and iodobutyl are preferable. In the formula, as preferable examples of the group X, a chlorine atom and a bromine atom may be mentioned. In particular, a chlorine atom is preferred. As preferable examples of the group R, a hydrogen atom, halogen atom, $C_1$ to $C_2$ lower alkyl group, $C_1$ to $C_2$ lower alkoxy group, and hydroxy group may be mentioned. In particular, a hydrogen atom, fluorine atom, chlorine atom, methyl group, and methoxy group are preferred.

IV) Process of Production of Benzoxazepine Derivative having Formula (V)

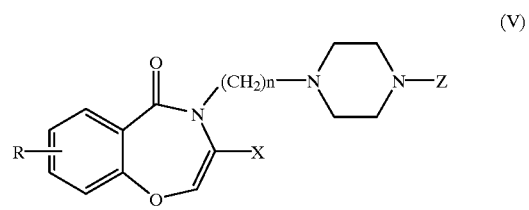
(V)

wherein n, R, X, and Z are as defined above.

The compound having the formula (V) may be produced by condensation of the benzoxazepine derivative having the formula (Ia) and the piperadine derivative having the formula (X):

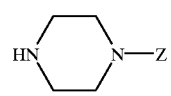
(X)

wherein Z is as defined above using, if necessary, a base such as triethylamine or a catalyst such as sodium iodide or other catalyst.

V) Process for Production of a Benzoxazepine Derivative having the Formula (VI)

The compound having the formula (VI)

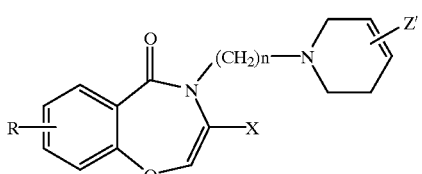
(VI)

wherein n, X, and R are as defined above, the dotted line indicates the presence or absence of a bond, and Z' indicates a heterocyclic group which may be substituted can be synthesized by condensation with an ordinary method of the benzoxazepine derivative having the formula (Ia) and the intermediate compound having the formula (XI):

(XI)

wherein, Z' is as defined above.

VI) Process of Production of Benzoxazepine Derivative having Formula (VIII)

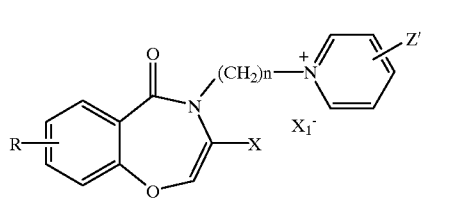

(VIII)

wherein, R, n, X, and Z' are as defined above, and $X_1$ indicates a halogen atom.

These are useful as synthetic intermediates of the benzoxazepine derivatives and their salts having formulas (Ib) or (VI).

The benzoxazepine derivative having formula (VIII) may be produced, for example, in the following way:

The benzoxazepine derivative having formula (Ia) may be condensed with the pyridine derivative having the formula (VII):

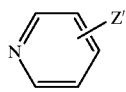

(VII)

wherein, Z' is as defined above by an ordinary method.

Specific embodiments of the compounds having the formulas (Ib), (V), and (VI) provided in accordance with the present invention will be explained in detail below using the Examples, but of course the present invention is not limited to these Examples.

In the compounds having the formulas (Ib) and (V) and (VI), as preferable examples of the integers n in the formulas, 3 to 5 may be mentioned. In particular, 4 is preferred. As preferable examples of the group X in the formulas (Ib) and (V) and (VI), a chlorine atom and bromine atom may be mentioned. In particular, a chlorine atom is preferable. As preferable examples of the group R, a hydrogen atom, halogen atom, $C_1$ to $C_2$ lower alkyl group, $C_1$ to $C_2$ lower alkoxy group, and hydroxy group may be mentioned. In particular, a hydrogen atom, fluorine atom, chlorine atom, methyl group, and methoxy group are more preferred. Further, as preferable examples of the group Z, a monocyclic or polycyclic aromatic group or heterocyclic group, selected from a phenyl group, naphthyl group, pyridyl group, pyrimidinyl group, pyradinyl group, pyridazinyl group, quinolyl group, isoquinolyl group, quinoxalinyl group, quinazolinyl group, 2-thiazolyl group, 2-oxazolyl group, 2-benzothiazolyl group, 2-benzoxazolyl group, 3-isothiazolyl group, 2-thienyl group, and 3-thienyl group substitutable with hydrogen, $C_1$ to $C_4$ lower alkyl group, $C_1$ to $C_4$ lower alkoxy group, hydroxy group, amino group, and/or halogen atom, may be mentioned. In particular, a group selected from phenyl group, naphthyl group, pyridyl group, pyrimidinyl group, quinoxalinyl group, quinolyl group, isoquinolyl group, and quinazolinyl group, substitutable with hydrogen, a methyl group, methoxy group, hydroxy group, amino group, chlorine atom, and/or fluorine atom is preferred. Further, as preferable examples of the group Z', hydrogen, a monocyclic or polycyclic heterocyclic group, substitutable with a $C_1$ to $C_4$ lower alkyl group, $C_1$ to $C_4$ lower alkoxy group, hydroxy group, amino group, and/or a halogen atom selected from a pyridyl group, pyrimidinyl group, pyradinyl group, pyridazinyl group, quinolyl group, isoquinolyl group, quinoxalinyl group, quinazolinyl group, 2-thiazolyl group, 2-oxazolyl group, 2-benzothiazolyl group, 2-benzoxazolyl group, 3-isothiazolyl group, 2-thienyl group, and 3-thienyl group may be mentioned. In particular, a group selected from pyridyl group, pyrimidinyl group, quinoxalinyl group, quinolyl group, isoquinolyl group, and quinazolinyl group, substitutable with hydrogen, a methyl group, methoxy group, hydroxy group, amino group, chlorine atom, and/or fluorine atom is preferred.

The intermediate usable for the production of the compound having the formula (VI), that is, the compound having the formula (XI), may be synthesized as follows. That is, of the compounds (XI), the pyrimidine derivative having the formula (XII):

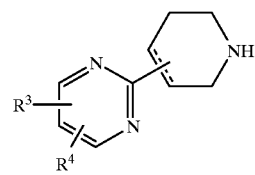

(XII)

wherein, $R^3$ and $R^4$ independently indicate a hydrogen atom, halogen atom, $C_1$ to $C_4$ lower alkyl group, or hydroxyl group is, for example, obtained as follows. The pyrimidine derivative (XIIa) where, in general formula (XII), for example, $R^3$ and $R^4$ respectively indicate hydrogen atoms, the dotted line indicates the presence of a bond, and the 2-pyrimidinyl group is bonded at the 4-position or 5-position of the 1,2,3,6-tetrahydropyridyl group:

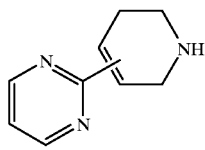

(XIIa)

is obtained by first converting the known compound of 2-chloropyrimidine to 2-tri-n-butyltinpyrimidine according to the method described in the document of J. Sandosham et al. (Tetrahedron, vol. 50, p. 275, 1994) or a similar method, then converting it to a lithium pyrimidinyl derivative according to the method described in that document or a similar method. Next, this is made to react with a piperidone derivative having the formula (XIII) or (XIV):

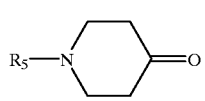
(XIII)

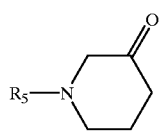
(XIV)

wherein, $R^5$ indicates a t-butoxycarbonyl group, ethoxycarbonyl group, or acetyl group to obtain a piperidylpyrimidine derivative having the formula (XV):

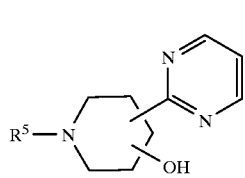
(XV)

wherein, $R^5$ is as defined above, when the 2-pyrimidinyl group is bonded at the 3-position of the piperidyl group, the hydroxy group is bonded at the 3-position of the piperidyl group, when the 2-pyrimidinyl group is bonded at the 4-position of the piperidyl group, the hydroxy group is bonded at the 4-position of the piperidyl group.

The obtained piperidylpyrimidine derivative (XV) is reacted with an acid chloride derivative such as thionyl chloride, methanesulfonyl chloride, trifluoromethansulfonyl chloride, phosphorus oxychloride, if necessary, in the presence of a base such as triethylamine or pyridine or reacted with Burgess reagent (described in E. M. Burgess et al., J. Org. Chem., vol. 38, p. 26, 1973) to obtain a tetrahydropyrimidine derivative having the formula (XV'):

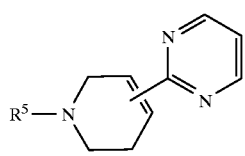
(XV')

wherein, $R^5$ is as defined above, and the 2-pyrimidinyl group in the formula is bonded at the 4-position or 5-position of the 1,2,3,6-tetrahydropyridyl group.

Next, if the compound is treated with an acid such as a trifluoroacetic acid, it is possible to obtain a useful synthetic intermediate where in the formula (XII), $R^3$ and $R^4$ respectively indicate a hydrogen atom and the dotted line indicates the presence of a bond, that is, a 2-(1,2,3,6-tetrahydropyridyl) pyrimidine derivative (XIIa).

Further, the synthetic intermediate (XIIa) can be obtained with treating the piperidylpyrimidine derivative having the formula (XV) directly with an acid such as trifluoroacetic acid.

The pyrimidine derivative (XIIb) where, in the formula (XII), for example, $R^3$ and $R^4$ respectively indicate a hydrogen atom, the dotted line indicates the absence of a bond, and the 2-pyrimidinyl group is bonded at the 3-position or 4-position of the piperidine group can be synthesized as follows:

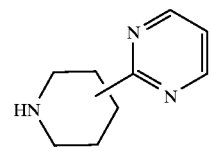
(XIIb)

That is, the tetrahydropyridylpyrimidine derivative having the general formula (XV') is hydrogenated in the presence of a palladium/carbon catalyst to obtain the piperidylpyrimidine derivative having the formula (XVa):

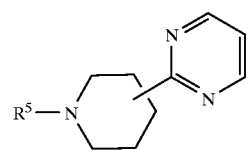
(XVa)

wherein, $R^5$ is the same as defined above, and the bond of the 2-pyrimidinyl group and piperidyl group in the formula is at the 3-position or 4-position.

The obtained piperidylpyrimidine derivative (XVa) may be treated with an acid such as trifluoroacetic acid to obtain the useful synthetic intermediate 2-piperidylpyrimidine derivative (XIIb).

Further, the 2-piperidylpyrimidine derivative (XIIb) can be obtained directly by catalytic reduction of the 2-(1,2,3, 6-tetrahydropyridyl)pyrimidine (XIIa).

Further, the pyrimidine derivative having the general formula (XII) can be synthesized in the following separate method. The compound having the formula (XIIa) in the formula (XII), for example, is obtained by first converting 3- or 4-cyanopyridine to 3- or 4-amidinopyridine according to the method described in the document of H. Fischer et al. (J. Heterocyclic Chem., vol. 17, p. 333, 1980) or a similar method. Next, this is subjected to a condensation dehydration reaction with malonaldehyde, malonaldehyde bis (dimethylacetal), etc. to obtain the pyrimidylpyridine derivative having the formula (XVI):

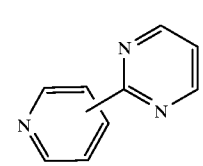
(XVI)

wherein, the 2-pyrimidinyl group is bonded at the 3-position or 4-position of the pyridine group.

Next, a substituent group $R^6$ is introduced to the pyridine ring to convert this to a compound having the formula (XVII):

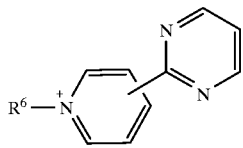
(XVII)

wherein, R⁶ indicates a $C_1$ to $C_4$ lower alkyl group, benzyl group, or methoxybenzyl group, X indicates a halogen atom, and the 2-pyrimidinyl group is bonded at the 3-position or 4-position of the pyridinium group.

Next, this is reduced with sodium borohydride to a compound having the formula (XVIII):

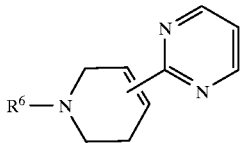
(XVIII)

wherein, R⁶ is as defined above, and the 2-pyrimidinyl group is bonded at the 4-position or 5-position of the 1,2,3,6-tetrahydropyridyl group.

Next, this is reacted with ethyl chloroformate, phenyl chloroformate, 1-chloroethyl chloroformate, 2-trimethylsilylethyl chloroformate, etc. to obtain the compound having the formula (XIX):

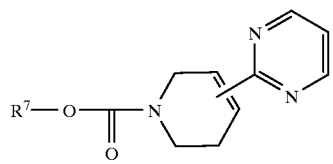
(XIX)

wherein, R⁷ indicates a $C_1$ to $C_4$ lower alkyl group, 1-chloroethyl group, phenyl group, or 2-trimethylsilylethyl group and the 2-pyrimidinyl group is bonded at the 4-position or 5-position of the 1,2,3,6-tetrahydropyridyl group.

The compound thus obtained may be decomposed with an alcohol such as methanol, ethanol, or hydrolyzed with an acid such as hydrochloric acid, acetic acid, sulfuric acid, bromic acid, or with a fluoride such as tetrabutylammonium fluoride (TBAF) to obtain the useful synthetic intermediate having the pyrimidinyl derivative (XIIa).

Further, in formula (XII), the formula (XIIb) is obtained by hydrogenating the compound having the formula (XVIII) in the presence of a palladium/carbon catalyst, if necessary, when adding an acid such as hydrochloric acid to obtain the compound having the formula (XVIIIa):

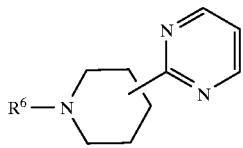
(XVIIIa)

wherein, R⁶ is as defined above, and the bond between the 2-pyrimidinyl group and piperidyl group is at the 3-position or 4-position. The compound thus obtained (XVIIIa) is reacted with ethyl chloroformate, phenyl chloroformate, 1-chloroethyl chloroformate, 2-trimethylsilylethyl chloroformate, etc. to obtain the compound having the formula (XIXa):

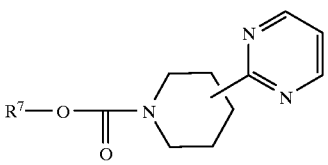
(XIXa)

wherein, R⁷ indicates a $C_1$ to $C_4$ lower alkyl group, 1-chloroethyl group, phenyl group, or 2-trimethylsilylethyl group, and the 2-pyrimidinyl group is bonded at the 3-position or 4-position of the piperidyl group. The compound thus obtained may be decomposed with an alcohol such as methanol, ethanol, or decomposed with a fluoride such as tetrabutylammonium fluoride (TBAF) or other fluoride to obtain the useful synthetic intermediate having the pyrimidine derivative (XIIb).

Further, the piperidylpyrimidine derivative (XIIb) may be obtained directly by catalytic reduction of the 1,2,3,6-tetrahydropyridylpyrimidine derivative having the formula (XIIa).

Further, the pyrimidine derivative (XIIc) where, in the formula (XII), for example, R³ indicates an alkyl group, for example, a methyl group, R⁴ indicates a hydrogen atom, the dotted line indicates the presence of a bond, and the 2-pyrimidinyl group is bonded at the 4-position or 5-position of the 1,2,3,6-tetrahydropyridyl group

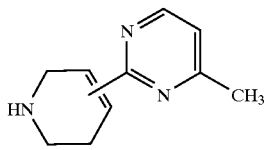
(XIIc)

can be synthesized by causing a condensation and dehydration reaction between 3- or 4-amidinopyridine and acetoaldehyde dimethyl acetal to obtain the compound of the formula (XX):

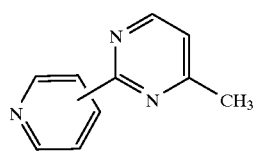

(XX)

then performing the same procedure as with the compound (XIIa).

Further, the pyrimidine derivative (XIId) where, in formula (XII), for example, $R^3$ indicates an alkyl group, for example, a methyl group, $R^4$ indicates a hydrogen atom, the dotted line indicates the absence of a bond, and the 2-pyrimidinyl group is bonded at the 3-position or 4-position of the piperidyl group

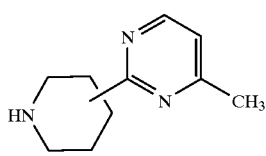

(XIId)

may be synthesized by hydrogenating the above pyrimidine derivative (XIIc) using, if necessary, an acid such as hydrochloric acid.

Further, the pyrimidine derivative (XIIe) where, in the formula (XII), for example, $R^3$ and $R^4$ indicate an alkoxy group, for example, a methoxy group, the dotted line indicates the presence of a bond, and the 2-pyrimidinyl group is bonded at the 4-position or 5-position of the 1,2,3,6-tetrahydropyridyl group

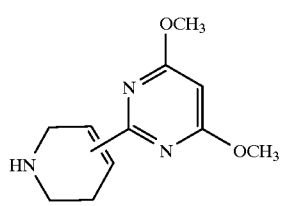

(XIIe)

may be synthesized by causing a condensation reaction between 3- or 4-amidinopyridine and malonyl dichloride to obtain the compound having the formula (XXI):

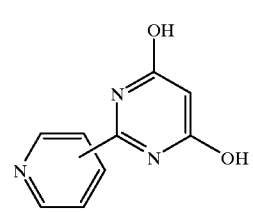

(XXI)

then dimethylating the resulting product to convert it to the compound (XXII):

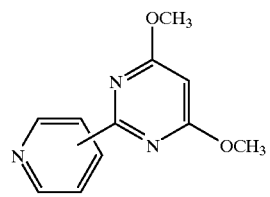

(XXII)

and then following the same procedure as with the compound (XIIa).

Further, the pyrimidine derivative (XIIf) where, in formula (XII), for example, $R^3$ indicates an alkyl group, for example, a methyl group, $R^4$ indicates a halogen, for example, a fluoro group, the dotted line indicates the presence of a bond, and the 2-pyrimidinyl group is bonded at the 4-position or 5-position of the 1,2,3,6-tetrahydropyridyl group

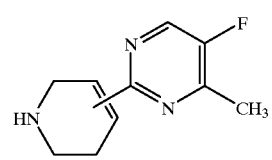

(XIIf)

may be synthesized by causing a condensation and dehydration reaction with 2-fluoro-3-oxo-butyroaldehyde dimethyl acetal to obtain a compound having the formula (XXIII):

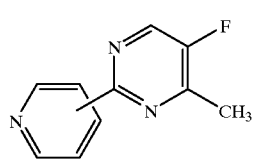

(XXIII)

then following the same procedure as the compound (XIIa).

In the intermediate compounds of the formula (XI), the pyridine derivative may be, for example, produced as follows. It may be obtained by the method described in the document of W. S. Saari et al. (J. Med. Chem., vol. 27, p. 1182, 1984) or a similar method.

Further, it may be obtained as follows as a separate method. That is, the pyridine derivative (XIa) where, in the formula (XI), for example, Z' indicates a 2-pyridyl group, the dotted line indicates the presence of a bond, and the 2-pyridyl group is bonded at the 4-position or 5-position of the 1,2,3,6-tetrahydropyridyl group

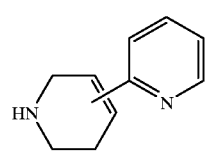

(XIa)

may be synthesized by first converting the known compound 2,4'-dipyridyl or 2,3'-dipyridyl to the compound of the formula (XVIIa) in accordance with the method described in the document of H. Fischer et al. (J. Heterocyclic Chem., vol. 17, p. 333, 1980) or a similar method:

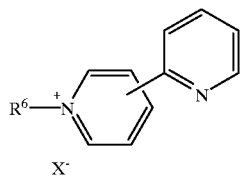

(XVIIa)

wherein, $R^6$ indicates a $C_1$ to $C_4$ lower alkyl group, benzyl group, or methoxybenzyl group, X indicates a halogen atom, and the 2-pyridyl group is bonded at the 3-position or 4-position of the pyridinium group.

Next, this is reduced with sodium borohydride to obtain the compound having the formula (XVIIIb):

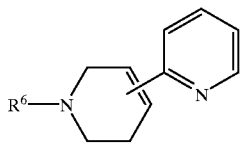

(XVIIIb)

wherein, $R^6$ is the same as defined above, and the 2-pyridyl group is bonded at the 4-position or 5-position of the 1,2,3,6-tetrahydropyridyl group.

Next, this is reacted with ethyl chloroformate, phenyl chloroformate, 1-chloroethyl chloroformate, or 2-trimethylsilylethyl chloroformate, etc. to obtain the compound having the formula (XIXb):

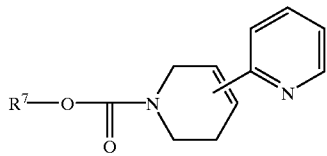

(XIXb)

wherein, $R^7$ indicates a $C_1$ to $C_4$ lower alkyl group, 1-chloroethyl group, phenyl group, or 2-trimethylsilylethyl group, and the 2-pyridyl group is bonded at the 4-position or 5-position of the 1,2,3,6-tetrahydropyridyl group. The compound obtained may be decomposed by methanol, ethanol, or other alcohol, hydrolyzed with an acid such as hydrochloric acid, acetic acid, sulfuric acid, hydrobromic acid, or decomposed with a fluoride such as tetrabutylammonium fluoride (TBAF) to obtain the useful synthetic intermediate having the pyridine derivative (XIa).

Further, the pyridine derivative (XIb) where, in the formula (XI), for example, Z' indicates a 2-pyridyl group, the dotted line indicates the absence of a bond, and the 2-pyridyl group is bonded at the 3-position or 4-position of the piperidyl group

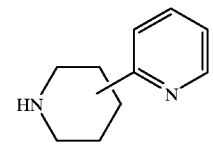

(XIb)

may be synthesized by hydrogenating the compound having the above formula (XVIIIb) in the presence of pd/c, while, if necessary adding an acid such as hydrochloric acid, to derive the compound having the formula (XVIIId):

(XVIIId)

wherein, $R^6$ is the same as defined above, and the 2-pyridyl group is bonded at the 3-position or 4-position of the piperidinyl group. Next, this is reacted with ethyl chloroformate, phenyl chloroformate, 1-chloroethyl chloroformate, 2-trimethylsilylethyl chloroformate, etc. to obtain the compound having the general formula (XIXd):

(XIXd)

wherein, $R^7$ indicates a $C_1$ to $C_4$ lower alkyl group, 1-chloroethyl group, phenyl group, or 2-trimethylsilylethyl group, and the 2-pyridyl group is bonded at the 3-position or 4-position of the piperidyl group. The obtained compound (XIXd) may then be decomposed with an alcohol such as methanol, ethanol, hydrolyzed with an acid such as hydrochloric acid, acetic acid, sulfuric acid, bromic acid, or decomposed with a fluoride such as tetrabutylammonium fluoride (TBAF) to obtain the useful synthetic intermediate having the pyridyl derivative (XIb).

Further, the piperidylpyridine derivative (XIb) may be obtained directly by catalytic reduction of the 1,2,3,6-tetrahydropyridine derivative having the above formula (XIa).

The compound having the final compound (VI) may be produced by substitution condensation of the synthetic intermediate of the formula (XI), for example, the synthetic intermediate pyrimidine derivative (XII) such as illustrated in the above (XIIa to XIIf), or the synthetic intermediate pyridine derivative such as illustrated in the above (XIa to XIb) with the synthetic intermediate (Ia), if necessary, using a base such as triethylamine, potassium carbonate, or a catalyst such as sodium iodide.

Synthesis of Final Compound having Formula (VI) by Separate Method

Further, the compound having the final compound (VI) may be synthesized through the compound (XXIV) where, in the formula (VIII), Z' is the following formula (XXV):

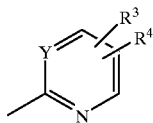
(XXV)

wherein Y indicates CH or a nitrogen atom, $R^3$ and $R^4$ respectively indicate a hydrogen atom, halogen atom, $C_1$ to $C_4$ lower alkyl group, or hydroxy group

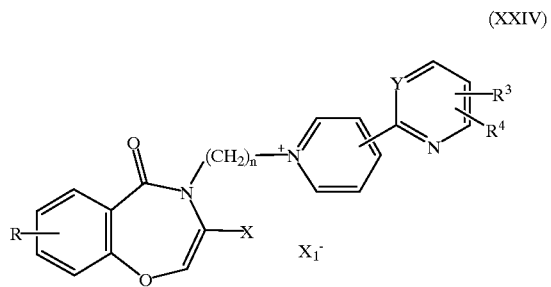
(XXIV)

wherein, X, R, $R^3$, $R^4$, Y, $X_1$, and n are the same as defined above.

Here, the synthetic intermediate having the formula (XXIV) may be synthesized as follows. That is, it is possible to obtain the useful synthetic intermediate having the above formula (XXIV) by causing a 2,3'-dipyridyl derivative, 2,4'-dipyridyl derivative, or the pyrimidinylpyridine derivative having the above formula (XVI) with the compound having the above formula (Ia) in the presence of sodium iodide.

It is also possible to produce the compound having the final compound (VI) by reducing the obtained synthetic intermediate (XXIV) with sodium borohydride.

EXAMPLES

The present invention will now be explained in further detail using Examples, but the present invention is of course not limited in scope by these Examples.

Example 1

Synthesis of 4-(4-chlorobutyl)-5-oxo-4,5-dihydro-1 4-benzoxazepin-3-yl diethyl phosphate 30 g of 4-(4-chlorobutyl)-2,3,4,5-tetrahydro-1,4-benzoxazepine-3,5-dione and 17.4 ml (1.1 equivalents) of diethyl chlorophosphate were dissolved in 180 ml of tetrahydrofuran, then 112 ml of 1N sodium bis (trimethylsilyl)amide was dropwise added at −50° C. under a stream of argon gas. After 1 hour, water was added and extraction performed by ethyl acetate. The organic layer was washed with saturated saline, then was dried over anhydrous magnesium sulfate. The solvent was distilled off to obtain 46 g of the above-identified compound (yield 100%). The product was sufficiently pure, but may be purified, if necessary, with silica gel column chromatography.

Example 2

Synthesis of 3-chloro-4-(4-chlorobutyl)-4,5-dihydro-1 4-benzoxazepin-5-one 46 g of the compound of Example 1 was dissolved in 250 ml of acetonitrile, then 44 g (1.3 equivalents) of triphenylphosphine chlorine complex was added and the mixture agitated overnight. The reaction solution was condensed under vacuum and then 500 ml of diisopropyl ether and 500 ml of 10% sodium hydroxide aqueous solution were added to the residue. The precipitated insolubles were removed by filtration. The filtrate was washed 3 times by a 10% aqueous sodium hydroxide solution and washed with saturated saline. This was dried over anhydrous magnesium sulfate, then the solvent was distilled off to obtain 30 g of the above-referenced compound (yield 96%). The product was sufficiently pure, but may be purified, if necessary, by silica gel column chromatography.

Example 3

Synthesis of 3-bromo-4-(4-chlorobutyl) 4,5-dihydro-1,4-benzoxazepin-5-one 4.6 g of the compound of Example 1 and 6.6 g (2 equivalents) of carbon tetrabromide were dissolved in 10 ml of methylene chloride, then 5.2 g (2 equivalents) of triphenylphosphine was added and the mixture agitated overnight. Water was added and extraction performed by chloroform. The resultant product was washed by saturated saline, then dried over anhydrous magnesium sulfate. The solvent was distilled off to obtain a crude product which was purified by silica gel column chromatography (hexane:ethyl acetate=4:1) to obtain 1.5 g of the above-referenced compound (yield 45%).

Example 4

Synthesis of 3-chloro-4-(4-chlorobutyl)-4,5-dihydro-1,4-benzoxazepin-5-one (separate method of synthesis of same substance as Example 2)

600 mg of the compound of Example 1 was dissolved in 10 ml of methylene chloride, then 470 mg (2 equivalents) of diethyl chlorophosphite was added and the mixture agitated for 3 hours. Water was added and extraction performed with chloroform. The resultant product was washed two times with a 10% aqueous sodium hydroxide solution and then washed with saturated saline. This was dried over anhydrous magnesium sulfate, then the solvent was distilled off to obtain 350 mg of the above-referenced compound (yield 82%). The product was sufficiently pure, but may be purified, if necessary, by silica gel column chromatography.

Example 5

Synthesis of 3-chloro-4,5-dihydro-4-(4-(4-(2-pyridyl) pyridinio-1-yl)butyl)-1,4-benzoxazepin-5-one chloride 200 mg of the compound of Example 2 was dissolved in 2 ml of acetone, then 21 mg (2 equivalents) of sodium iodide and 120 mg (1.1 equivalents) of 2,4'-dipyridine were added and the mixture heated and refluxed for 30 hours. The mixture was then allowed to cool, then the precipitated crystals were obtained by filtration. Recrystallization was performed with a mixed solvent of methanol, acetone, and ether to obtain 298 mg of the above-referenced compound (yield 96%).

Example 6

Synthesis of 3-chloro-4,5-dihydro-4-(4-(4-(2-pyrimidinyl)pyridinio-1-yl)butyl)-1,4-benzoxazepin-5-one chloride 500 mg of the compound of Example 2 was dissolved in 10 ml of acetone, then 390 mg (1.5 equivalents) of sodium iodide and 330 mg (1.1 equivalents) of 4-(2-pyrimidyl) pyridine were added and the mixture heated and refluxed for 48 hours. The mixture was then allowed to cool, then the precipitated crystals were obtained by filtration. Recrystallization was performed with acetone to obtain 860 mg of the above-referenced compound (yield 100%).

Example 7

Synthesis of 4-(2-pyridinyl)-1,2,3,6-tetrahydropyridine (1)

Step 1) Synthesis of N-t-butoxycarbonyl-4-hydroxy-4-(2-pyrimidinyl)piperidine 4.74 g of 2-tri-n-butyltinpyrimidine was dissolved in 30 ml of tetrahydrofuran (hereinafter referred to as THF), then 12 ml (1.5 equivalents) of 1.6N n-butyllithium/hexane solution was added dropwise in a stream of nitrogen gas at −78° C. After 30 minutes, 30 ml of a THF solution of 3.06 g (1.2 equivalents) of N-t-butoxycarbonyl-4-piperidone was dropwise added, then the reaction temperature was gradually raised to room temperature. Ice water was added to the reaction solution then extraction was performed with ethyl acetate. The resultant product was washed with water and saturated saline, then dried over anhydrous magnesium sulfate. The solvent was distilled off to obtain a crude product which was then purified by silica gel column chromatography (hexane:ethyl acetate=2:1) to obtain 1.10 g of the above-referenced compound (yield 26%).

Step 2) Synthesis of N-t-butoxycarbonyl-4-(2-pyrimidinyl)-1,2,3,6-tetrahydropyridine 2.11 g of the compound of Step 1 of Example 7 was dissolved in 30 ml of pyridine, then 1.0 ml (1.4 equivalents) of phosphorous oxychloride was added under ice cooling and the resultant product was agitated for 15 hours. The pyridine was distilled off under reduced pressure, then a 10% aqueous sodium hydroxide solution was added and extraction performed with methylene chloride. The organic layer was washed with saturated saline, then was dried over anhydrous magnesium sulfate. The solvent was distilled off to obtain a crude product which was then purified by silica gel column chromatography (hexane:ethyl acetate=2:1) to obtain 1.01 g of the above-referenced compound (yield 51%).

Step 3) Synthesis of 4-(2-pyrimidinyl)-1,2,3-6-tetrahydropyridine 500 mg of the compound of Step 2 of Example 7 was dissolved in 10 ml of methylene chloride, then 3.5 ml of trifluoroacetic acid (hereinafter referred to as TFA) was added and the resultant product agitated at room temperature for 30 minutes. This was concentrated, then a 10% aqueous sodium hydroxide solution was added and extraction performed with chloroform. The organic layer was washed with saturated saline, then dried over anhydrous magnesium sulfate. The chloroform solution was concentrated to obtain 260 mg of the above-referenced compound (yield 87%).

Example 8

Synthesis of 4-(2-pyrimidinyl)piperidine

Step 1) Synthesis of N-t-butoxycarbonyl-4-(2-pyrimidinyl)piperidine 490 mg of the compound of Step 2 of Example 7 was dissolved in 10 ml of ethanol, then 100 mg of 10% palladium carbon was added and the resultant product agitated under a stream of hydrogen gas for 2 days. The catalyst was filtered off and the ethanol distilled off. The residue was purified by silica gel column chromatography (hexane:ethyl acetate= 1:1) to obtain 160 mg of the above-referenced compound (yield 33%).

Step 2) Synthesis of 4-(2-pyrimidinyl)piperidine 1.5 g of the compound of Step 1 of Example 8 was dissolved in 30 ml of methylene chloride, then 10 ml of TFA was added and the resultant product agitated at room temperature for 30 minutes. The same procedure was then followed as in Step 3 of Example 6 to obtain 750 mg of the above-referenced compound (yield 82%).

Example 9

Synthesis of 4-(2-pyrimidinyl)-1,2,3,6-tetrahydropyridine (2)

Step 1) Synthesis of 4-(2-pyrimidinyl)pyridine 35 mg (0.04 equivalent) of sodium was dissolved in 5 ml of methanol, then 4.0 g of 4-cyanopyridine was added. After 30 minutes, 2.0 g (1 equivalent) of ammonium chloride was added and the resultant product agitated for 24 hours. The solution was concentrated to about half, then 5 ml of acetone was added. The precipitated crystal was obtained by filtration to obtain 4-amidinopyridine chlorate. This was dissolved in 2.2 ml (5 equivalents) of water, then 5.0 ml (1.2 equivalents) of 1,1,3,3-tetramethoxypropane and 1.4-dioxane (2 ml) were added and the resultant product agitated at 130° C. for 1 hour to dry it to a solid. This was allowed to cool, then a 10% aqueous sodium hydroxide solution was added and extraction performed by ethyl acetate. The resultant product was washed with water and saturated saline, then dried over anhydrous magnesium sulfate. The solvent was distilled off to obtain 2.58 g of the above-referenced compound (yield 65%).

Step 2) Synthesis of 1-benzyl-4-(2-pyrimidinyl)-1,2,3,6-tetrahydropyridine 652 mg of the compound of Step 1 of Example 9 was dissolved in 10 ml of acetonitrile, then 0.96 ml (2 equivalents) of benzylchloride was added and the resultant product heated and refluxed for 20 hours. This was concentrated, then the residue was recrystallized with a mixed solvent of acetonitrile and ether to obtain pyridinium. The resultant product was dissolved in ethanol (5 ml) and 307 mg (2 equivalents) of sodium borohydride was added. After 30 minutes, water was added and extraction performed with ethyl acetate. This was washed with water and saturated saline, then dried over anhydrous magnesium sulfate. The solvent was distilled off to obtain a product which was then purified by silica gel column chromatography (methylene chloride:methanol 30:1) to obtain 968 mg of the above-referenced compound (yield 95%).

Step 3) Synthesis of 4-(2-pyrimidinyl)-1,2,3-6-tetrahydropyridine 710 mg of the compound of step 2 of Example 9 was dissolved in 10 ml of dichloroethane, then 0.31 ml (1 equivalent) of 1-chloroethyl chlorocarbonate was added and the resultant product heated and refluxed for 1 hour. This was concentrated once, then methanol was added again and the resultant product heated and refluxed for 1 hour. This was concentrated, then recrystallized with a mixed solvent of methanol and ether to obtain 471 mg of a chloride of the above-referenced compound (yield 84%).

Example 10

Synthesis of 4-(4-methylpyrimidin-2-yl)-1,2,3,6-tetrahydropyridine

Step 1) Synthesis of 1-benzyl-4-(4-methylpyrimidin-2-yl)-1,2,3,6-tetrahydropyridine 274 mg of 4-(4-methylpyrimidin-2-yl)pyridine was dissolved in 5 ml of acetonitrile, then 0.40 ml (2 equivalents)

of benzylchloride was added and the resultant product heated and refluxed for 10 hours. This was concentrated, then the residue was recrystallized with a mixed solvent of acetonitrile and ether to obtain a pyridinium salt. This was dissolved in ethanol (3 ml) and 129 mg (2 equivalents) of sodium borohydride added. After 30 minutes, water was added and extraction performed by ethyl acetate. The same procedure was then followed as in step 2 of Example 9 for the reaction, treatment, and purification to obtain 409 mg of the above-referenced compound (yield 94%).

Step 2) Synthesis of 4-(4-methylpyrimidin-2-yl)-1,2,3,6-tetrahydropyridine 300 mg of the compound of Step 1 of Example 10 was dissolved in 5 ml of dichloroethane, then 0.14 ml (1 equivalent) of 1-chloroethyl chlorocarbonate was added and the resultant product heated and refluxed for 1 hour. This was concentrated once, then methanol was again added and the resultant product heated and refluxed for 1 hour. The resultant product was concentrated, then recrystallized with a mixed solvent of methanol and ether to obtain 213 mg of a chloride of the above-referenced compound (yield 88%).

Example 11

Synthesis of 5-(2-pyrimidinyl)-1,2,3,6-tetrahydropyridine

Step 1) Synthesis of N-t-butoxycarbonyl-3-hydroxy-3-(2-pyrimidinyl)piperidine 5.0 g of 2-tri-n-butyltinpyrimidine was dissolved in 60 ml of THF, then 12 ml (1.5 equivalents) of 1.7N n-butyllithium/hexane solution was dropwise added under a stream of nitrogen gas at −78° C. After 1 hour, 30 ml of a THF solution of 3.24 g (1.2 equivalents) of N-t-butoxycarbonyl-3-piperidone was dropwise added, then the reaction temperature was gradually raised to room temperature. Aqueous saturated ammonium chloride solution was added to this reaction solution and extraction performed with ethyl acetate. The resultant product was washed with water and saturated saline, then dried over anhydrous magnesium sulfate. The solvent was distilled off to obtain a product which was then purified by silica gel column chromatography (methylene chloride:methanol=20:1) to obtain 1.10 g of the above-referenced compound (yield 29%).

Step 2) Synthesis of N-t-butoxycarbonyl-5-(2-pyrimidinyl)-1,2,3,6-tetrahydropyridine 1.56 g of the compound of Step 1 of Example 11 was dissolved in 15 ml of pyridine, then 0.8 ml (1.5 equivalents) of phosphorus oxychloride was added under ice cooling and the resultant product agitated for 16 hours. The same procedure was followed as in Step 2 of Example 7 for the reaction, treatment, and purification to obtain 285 mg of the above-referenced compound (yield 20%).

Step 3) Synthesis of 5-(2-pyrimidinyl)-1,2,3,6-tetrahydropyridine 260 mg of the compound of Step 2 of Example 11 was dissolved in 5 ml of methylene chloride, then 2 ml of TFA was added and the resultant product agitated at room temperature for 30 minutes. The same procedure was followed as in Step 3 of Example 7 for the reaction, treatment, and purification to obtain 146 mg of the above-referenced compound (yield 91%).

Example 12

Synthesis of 3-(2-pyrimidinyl)piperidine

Step 1) Synthesis of N-t-butoxycarbonyl-3-(2-pyrimidinyl)piperidine 490 mg of the compound of Step 2 of Example 11 was dissolved in 10 ml of ethanol, then 40 mg of 10% palladium carbon was added and the resultant product agitated under a stream of hydrogen gas for 15 hours. The same procedure was followed as in Step 1 of Example 8 for the reaction, treatment, and purification to obtain 100 mg of the above-referenced compound (yield 50%).

Step 2) Synthesis of 3-(2-pyrimidinyl)piperidine 140 mg of the compound of Step 1 of Example 12 was dissolved in 5 ml of methylene chloride, then 2 ml of TFA was added and the resultant product agitated at room temperature for 30 minutes. The same procedure was followed as in Step 3 of Example 11 for the reaction, treatment, and purification to obtain 70 mg of the above-referenced compound (yield 81%).

Example 13

Synthesis of 3-chloro-4,5-dihydro-4-(3-(4-(2-pyrimidinyl)piperadin-1-yl)propyl)-1,4-benzoxazepin-5-one 200 mg of the 3-chloro-4-(3-chloropropyl)-4,5-dihydro-1,4-benzoxazepin-5-one synthesized by the method of Example 15 described in International Publication WO96/24594 was dissolved in 6 ml of dimethylformamide, then 180 mg (1.5 equivalents) of 1-(2-pyrimidinyl)piperadine, 220 mg (2 equivalents) of sodium iodide, and 0.21 ml (2 equivalents) of triethylamine were added and the resultant product agitated at 80° C. for 15 hours. This was allowed to cool, then water was added and extraction performed twice with ethyl acetate. The entire organic layer was washed with an aqueous saturated sodium bicarbonate solution and saturated saline, then dried over anhydrous magnesium sulfate. The solvent was distilled off to obtain a crude product which was then purified by silica gel column chromatography (methylene chloride:methanol=30:1) to obtain 140 mg of the above-referenced compound (yield 48%). Note that the chloride was obtained by making a chloride by an ordinary method, then recrystallizing from a mixed solvent of methanol and ether.

Example 14

Synthesis of 3-chloro-4,5-dihydro-4-(4-(4-(2-pyridyl)piperadin-1-yl)butyl)-1,4-benzoxazepin-5-one 287 mg of the compound of Example 2 was dissolved in 9 ml of dimethylformamide, then 0.24 ml (1.6 equivalents) of 1-(2-pyridyl)piperadine, 300 mg (2 equivalents) of sodium iodide, and 0.29 ml (2 equivalents) of triethylamine were added and the resultant mixture was agitated at 80° C. for 14 hours. The resultant mixture was treated and purified in the same way as Example 13 to obtain 167 mg of the above-referenced compound (yield 41%). Note that the fumarate was obtained by making a fumarate by an ordinary method, then recrystallizing from a mixed solvent of ethanol and diisopropyl ether.

Example 15

Synthesis of 3-chloro-4,5-dihydro-4-(4-(4-(4-quinazolyl)piperadin-1-yl)butyl)-1,4-benzoxazepin-5-one 429 mg (1.5 equivalents) of the compound of Example 2 was dissolved in 10 ml of dimethylformamide, then 214 mg of 1-(4-quinazolyl)piperadine, 300 mg (2 equivalents) of sodium iodide, and 0.28 ml (2 equivalents) of triethylamine were added and the resultant mixture agitated at 80° C. for 15 hours. This was treated and purified in the same way as Example 13 to obtain 380 mg of the above-referenced compound (yield 83%). Note that the chloride was obtained by making a chloride by an ordinary method, then recrystallizing by acetone.

Example 16

Synthesis of 3,8-dichloro-4,5-dihydro-4-(4-(4-(2-pyridyl)piperadin-1-yl)butyl)-1,4-benzoxazepin-5-one 169 mg of the 4-(4-chlorobutyl)-3,8-dichloro-4,5-dihydro-1,4-benzoxazepin-5-one synthesized by the method of Example 17 described in International Publication WO96/24594 was dissolved in 3 ml of dimethylformamide, then 129 mg (1.5 equivalents) of 1-(2-pyridyl)piperadine, 158 mg (2 equivalents) of sodium iodide, and 106 mg (2 equivalents) of triethylamine were added and the resultant mixture agitated at 80° C. for 6 hours. This was treated and refined in the same way as Example 13 to obtain 219 mg of the above-referenced compound (yield 93%). Note that the dichloride was obtained by making a dichloride by an ordinary method, then recrystallizing from a mixed solvent of methanol, chloroform, and ether.

Example 17

Synthesis of 3-chloro-4,5-dihydro-7-methyl-4-(4-(4-(2-pyrimidinyl)piperadin-1-yl)butyl)-1,4-benzoxazepin-5-one 129 mg of the 3-chloro-4-(4-chlorobutyl)-4,5-dihydro-7-methyl-1,4-benzoxazepin-5-one synthesized by the method of Example 19 described in International Publication WO96/24594 was dissolved in 2 ml of dimethylformamide, then 106 mg (1.5 equivalents) of 1-(2-pyrimidinyl)piperadine, 129 mg (2 equivalents) of sodium iodide, and 87 mg (2 equivalents) of triethylamine were added and the resultant mixture agitated at 90° C. for 7 hours. This was then treated and purified in the same way as Example 13 to obtain 152 mg of the above-referenced compound (yield 83%). Note that the dichloride was obtained by making a dichloride by an ordinary method, then recrystallizing from ether.

Example 18

Synthesis of 3-chloro-4,5-dihydro-4-(4-(4-(2-pyrimidinyl)-1,2,3,6-tetrahydropyridin-1-yl)butyl)-1,4-benzoxazepin-5-one 128 mg of the compound of Example 7 was dissolved in 10 ml of DMF, then 335 mg (1.5 equivalents) of the compound of Example 2, 238 mg (2 equivalents) of sodium iodide, and 0.22 ml (2 equivalents) of triethylamine were added and the resultant mixture agitated at 80° C. for 14 hours. This was treated and purified in the same way as Example 13 to obtain 86 mg of the above-referenced compound (yield 26%). Note that the chloride was obtained by making a chloride by an ordinary method, then recrystallizing from a mixed solvent of methanol and acetone.

Example 19

Synthesis of 3-chloro-4,5-dihydro-4-(4-(4-(2-pyrimidinyl)piperidin-1-yl)butyl)-1,4-benzoxazepin-5-one 46 mg of the compound of Example 8 was dissolved in 5 ml of DMF, then 120 mg (1.5 equivalents) of the compound of Example 2, 84 mg (2 equivalents) of sodium iodide, and 0.08 ml (2 equivalents) of triethylamine were added and the resultant mixture agitated at 80° C. for 12 hours. This was treated and purified in the same way as Example 13 to obtain 98 mg of the above-referenced compound (yield 84%). Note that the chloride was obtained by making a chloride by an ordinary method, then recrystallizing from a mixed solvent of methanol and acetone.

Example 20

Synthesis of 3-chloro-4,5-dihydro-4-(4-(5-(2-pyrimidinyl)-1,2,3,6-tetrahydropyridin-1-yl)butyl)-1,4-benzoxazepin-5-one 70 mg of the compound of Example 11 was dissolved in 8 ml of DMF, then 150 mg (1.2 equivalents) of the compound of Example 2, 156 mg (2.4 equivalents) of sodium iodide, and 0.15 ml (2.4 equivalents) of triethylamine were added and the resultant mixture agitated at 80° C. for 13 hours. This was treated and purified in the same way as Example 13 to obtain 36 mg of the above-referenced compound (yield 20%). Note that the fumarate was obtained by making a fumarate by an ordinary method, then recrystallizing from acetone.

Example 21

Synthesis of 3,8-dichloro-4,5-dihydro-4-(4-(4-(2-pyrimidinyl)-1,2,3,6-tetrahydropyridin-1-yl)butyl)-1,4-benzoxazepin-5-one 50 mg of the compound of Example 9 was dissolved in 5 ml of DMF, then 66 mg (1.5 equivalents) of the starting compound used in Example 16, 62 mg (2 equivalents) of sodium iodide, and 42 mg (2 equivalents) of triethylamine were added and the resultant mixture agitated at 90° C. for 6 hours. This was treated and purified in the same way as Example 13 to obtain 39 mg of the above-referenced compound (yield 43%). Note that the fumarate was obtained by making a fumarate by an ordinary method, then recrystallizing from a mixed solvent of methanol and ether.

Example 22

Synthesis of 3,8-dichloro-4,5-dihydro-4-(4-(4-(2-pyrimidinyl)piperidin-1-yl)butyl)-1,4-benzoxazepin-5-one 70 mg of the compound of Example 8 was dissolved in 5 ml of DMF, then 206 mg (1.5 equivalents) of the starting compound used in Example 16, 145 mg (2.3 equivalents) of sodium iodide, and 97 mg (2.3 equivalents) of triethylamine were added and the resultant mixture agitated at 90° C. for 6 hours. This was treated and purified in the same way as Example 13 to obtain 177 mg of the above-referenced compound (yield 92%). Note that the fumarate was obtained by making a fumarate by an ordinary method, then recrystallizing from ether and making an amorphous powder.

Example 23

Synthesis of 3-chloro-4,5-dihydro-8-methoxy-4-(4-(4-(2-pyrimidinyl)-1,2,3,6-tetrahydropyridin-1-yl)butyl)-1,4-benzoxazepin-5-one 70 mg of the compound of Example 9 was dissolved in 6 ml of DMF, then 150 mg (1.1 equivalents) of 3-chloro-4-(4-chlorobutyl)-4,5-dihydro-8-methoxy-1,4-benzoxazepin-5-one synthesized by the method of Example 18 described in International Publication WO 96/24594, 142 mg (2.2 equivalents) of sodium iodide, and 0.13 ml (2.2 equivalents) of triethylamine were added and the resultant mixture agitated at 80° C. for 14 hours. This was treated and purified in the same way as Example 13 to obtain 60 mg of the above-referenced compound (yield 32%). Note that the fumarate was obtained by making a fumarate by an ordinary method, then recrystallizing from ether.

Example 24

Synthesis of 3-chloro-4,5-dihydro-8-methoxy-4-(4-(4-(2-pyrimidinyl)piperidin-1-yl)butyl)-1,4-benzoxazepin-5-one 70 mg of the compound of Example 8 was dissolved in 6 ml of DMF, then 150 mg (1.1 equivalents) of the 3-chloro-4-(4-chlorobutyl)-4,5-dihydro-8-methoxy-1,4-benzoxazepin-5-one synthesized by the method of Example 18 described in International Publication WO 96/24594, 142 mg (2.2 equivalents) of sodium iodide, and 0.13 ml (2.2 equivalents) of triethylamine were added and the resultant mixture agitated at 80° C. for 15 hours. This was treated and purified in the same way as Example 13 to obtain 177 mg of the above-referenced compound (yield 92%). Note that the fumarate was obtained by making a fumarate by an ordinary method, then recrystallizing from acetone and ether.

Example 25

Synthesis of 3,8-dichloro-4,5-dihydro-4-(4-(4-(2-pyridyl)-1,2,3,6-tetrahydropyridin-1-yl)butyl)-1,4-benzoxazepin-5-one 200 mg of the starting compound used in Example 16 was dissolved in 5 ml of DMF, then 120 mg (1.2 equivalents) of 4-(2-pyridyl)-1,2,3,6-tetrahydropyridine, 187 mg (2 equivalents) of sodium iodide, and 0.17 ml (2 equivalents) of triethylamine were added and the resultant mixture agitated at 90° C. for 18 hours. This was treated and purified in the same way as Example 13 to obtain 117 mg of the above-referenced compound (yield 43%). Note that the fumarate was obtained by making a fumarate by an ordinary method, then recrystallizing from a mixed solution of methanol and ether.

Example 26

Synthesis of 3,8-dichloro-4,5-dihydro-4-(4-(4-(2-pyridyl)piperidin-1-yl)butyl)-1,4-benzoxazepin-5-one 200 mg of the starting compound used in Example 16 was dissolved in 5 ml of DMF, then 149 mg (1.2 equivalents) of 4-(2-pyridyl)piperidine chlorate, 187 mg (2 equivalents) of sodium iodide, and 0.30 ml (3.5 equivalents) of triethylamine were added and the resultant mixture agitated at 90° C. for 20 hours. This was treated and purified in the same way as Example 13 to obtain 158 mg of the above-referenced compound (yield 59%). Note that the fumarate was obtained by making a fumarate by an ordinary method, then recrystallizing from a mixed solvent of methanol and ether.

Example 27

Synthesis of 3-chloro-4,5-dihydro-4-(3-(4-(2-pyridyl)-1,2,3,6-tetrahydropyridin-1-yl)propyl)-1,4-benzoxazepin-5-one 200 mg of the starting compound used in Example 13 was dissolved in 5 ml of DMF, then 141 mg (1.2 equivalents) of 4-(2-pyridyl)-1,2,3,6-tetrahydropyridine, 220 mg (2 equivalents) of sodium iodide, and 0.21 ml (2 equivalents) of triethylamine were added and the resultant mixture agitated at 90° C. for 18 hours. This was treated and purified in the same way as Example 13 to obtain 150 mg of the above-referenced compound (yield 52%). Note that the fumarate was obtained by making a fumarate by an ordinary method, then recrystallizing from a mixed solvent of methanol and ether.

Example 28

Synthesis of 3-chloro-4,5-dihydro-4-(3-(4-(2-pyridyl)piperidin-1-yl)-propyl)-1,4-benzoxazepin-5-one 200 mg of the starting compound used in Example 13 was dissolved in 5 ml of DMF, then 175 mg (1.2 equivalents) of 4-(2-pyridyl)piperidine chlorate, 220 mg (2 equivalents) of sodium iodide, and 0.36 ml (3.5 equivalents) of triethylamine were added and the resultant mixture agitated at 90° C. for 20 hours. This was treated and purified in the same way as Example 13 to obtain 160 mg of the above-referenced compound (yield 55%). Note that the fumarate was obtained by making a fumarate by an ordinary method, then making an amorphous powder.

Example 29

Synthesis of 3-chloro-4,5-dihydro-4-(5-(4-(2-pyridyl)-1,2,3,6-tetrahydropyridin-1-yl)pentyl)-1,4-benzoxazepin-5-one 250 mg of the compound of the 3-chloro-4-(5-bromopentyl)-4,5-dihydro-1,4-benzoxazepine-5-one synthesized by the method described in Example 20 of International Publication WO96/24594 was dissolved in 5 ml of acetonitrile, then 139 mg (1.2 equivalents) of 4-(2-pyridyl)-1,2,3,6-tetrahydropyridine and 0.20 ml (2 equivalents) of triethylamine were added and the resultant mixture heated and refluxed for 8 hours. This was treated and refined in the same way as Example 13 to obtain 110 mg of the above-referenced compound (yield 37%). Note that the fumarate was obtained by making a fumarate by an ordinary method, then recrystallizing from a mixed solvent of methanol and ether.

Example 30

Synthesis of 3-chloro-4,5-dihydro-4-(4-(4-((4-methyl)pyrimidin-2-yl)-1,2,3,6-tetrahydropyridin-1-yl)butyl)-1,4-benzoxazepin-5-one 200 mg of the compound of Example 2 was dissolved in 5 ml of DMF, then 178 mg (1.2 equivalents) of a chlorate of 4-(4-methylpyrimidin-2-yl)-1,2,3,6-tetrahydropyridine synthesized by the method described in Example 28 of International Publication WO96/24594, 210 mg (2 equivalents) of sodium iodide, and 0.34 ml (3.5 equivalents) of triethylamine were added and the resultant mixture agitated at 90° C. for 20 hours. This was treated and purified in the same way as Example 13 to obtain 154 mg of the above-referenced compound (yield 54%). Note that the fumarate was obtained by making a fumarate by an ordinary method, then recrystallizing from a mixed solvent of methanol and ether.

Example 31

Synthesis of 3-chloro-4,5-dihydro-4-(4-(4-(2-pyridyl)piperidin-1-yl)butyl)-1,4-benzoxazepin-5-one 550 mg of the compound of Example 2 was dissolved in 10 ml of DMF, then 210 mg (1.2 equivalents) of 4-(2-pyridyl)piperidine, 390 mg (2 equivalents) of sodium iodide, and 0.36 ml (2 equivalents) of triethylamine were added and the resultant mixture agitated at 90° C. for 17 hours. This was treated and purified in the same way as Example 13 to obtain 450 mg of the above-referenced compound (yield 85%). Note that the fumarate was obtained by making a fumarate by an ordinary method, then recrystallizing from acetone.

Example 32

Synthesis of 3-chloro-4,5-dihydro-4-(4-(4-(2-pyridyl)-1,2,3,6-tetrahydropyridin-1-yl)butyl)-1,4-benzoxazepin-5-one 487 mg of the compound of Example 2 was dissolved in 10 ml of DMF, then 180 mg (1.2 equivalents) of a 4-(2-pyridyl)-1,2,3,6-tetrahydropyridine, 336 mg (2 equivalents) of sodium iodide, and 0.31 ml (2 equivalents) of triethylamine were added and the resultant mixture agitated at 90° C. for 20 hours. This was treated and refined in the same way as Example 13 to obtain 290 mg of the above-referenced compound (yield 63%). Note that the acid addition salt was made a dichlorate by an ordinary method, then recrystallizing the crude product obtained from a mixed solvent of isopropyl alcohol and water (13:1). This was repeatedly recrystallized from the same mixed solvent to obtain a dichloride of the above-referenced compound (yield 66% from free amines).

Example 33

Synthesis of 3-chloro-4,5-dihydro-4-(4-(5-(2-pyridyl)-1,2,3,6-tetrahydropyridin-1-yl)butyl)-1,4-benzoxazepin-5-one 102 mg of the compound of Example 2 was dissolved in 2 ml of DMF, then 52 mg (0.9 equivalent) of 5-(2-pyridyl)-1,2,3,6-tetrahydropyridine, 107 mg (2 equivalents) of sodium iodide, and 66 mg (2 equivalents) of triethylamine were added and the resultant mixture agitated at 90° C. for 20 hours. This was treated and purified in the same way as Example 13 to obtain 65 mg of the above-referenced compound (yield 49%). Note that the fumarate was obtained by making a fumarate by an ordinary method, then making an amorphous powder.

Example 34

Synthesis of 3-chloro-4,5-dihydro-4-(4-(4-(2-pyrimidinyl)-1,2,3,6-tetrahydropyridin-1-yl)butyl)-1,4-benzoxazepin-5-one (Synthesis of the same compound of Example 18 by another method)

560 mg of the the 3-chloro-4,5-dihydro-4-(4-(4-(2-pyrimidinyl)pyridinio-1-yl)butyl)-1,4-benzoxazepin-5-one chloride described in Example 24 of International Publication WO96/24594 was dissolved in 15 ml of ethanol, then 98 mg (2 equivalents) of sodium borohydride was added under ice cooling and the resultant mixture agitated at room temperature for 10 minutes. Water was added and extraction performed with ethyl acetate. The organic layer was washed with water and saturated saline, then was dried over anhydrous magnesium sulfate. The solvent was distilled off to obtain a crude product which was then purified by silica gel column chromatography (methylene chloride:methanol=30:1) to obtain 462 mg of the above-referenced compound (yield 89%).

Example 35

Synthesis of 3-chloro-4,5-dihydro-4-(4-(4-(2-pyridyl)-1,2,3,6-tetrahydropyridin-1-yl)butyl)-1,4-benzoxazepin-5-one (synthesis of identical substance as Example 32 by different method)

800 mg of the compound of Example 5 was dissolved in 20 ml of ethanol, 140 mg (2 equivalents) of sodium borohydride was added under ice cooling, then the result was agitated at room temperature for 10 minutes. Water was added and extraction was performed with ethyl acetate. The organic layer was washed with water and saturated saline, then was dried with anhydrous magnesium sulfate. The solvent was distilled off and the resultant crude product was refined with silica gel column chromatography (methylene chloride:methanol=30:1), to obtain the above-referenced compound in an amount of 600 mg (yield of 81%).

TABLE I

| Example | Formula and Property | IR (cm$^{-1}$) | NMR (δppm) | Remarks |
|---|---|---|---|---|
| 1 | [structure: benzoxazepinone with N-(CH₂)₃-OP(=O)(OEt)₂ side chain] oil | 3007, 1703 1653, 1606 1456, 1393 1338, 1278 1152 (CHCl₃) | 7.85(1H, d, J=8Hz), 7.42(1H, t, J=8Hz), 7.21(1H, t, J=8Hz), 7.02(1H, d, J=8Hz), 6.86(1H, d, J=2Hz), 4.09–4.15(4H, m), 3.82–3.87(2H, m), 3.57–3.61(2H, m), 1.85–1.89(4H, m), 1.28(6H, t, J=7Hz) (CHCl₃) | 404 (FAB-MS) |
| 2 | [structure: benzoxazepinone with N-(CH₂)₃-Cl side chain, Cl on ring] oil | 2956, 1704 1644, 1605 1574, 1538 1479, 1236 (NaCl) | 7.86–7.89(1H, m), 7.43–7.47(1H, m), 7.22–7.26(1H, m), 7.02(1H, d, J=8Hz), 6.73(1H, s), 3.94(2H, t, J=6Hz), 3.57–3.60(2H, m), 1.86–1.89(4H, m) (CDCl₃) | 286 (FAB-MS) |
| 3 | [structure: benzoxazepinone with N-(CH₂)₃-Cl side chain, Br on ring] oil | 2958, 1704 1646, 1606 1566, 1533 1477 (NaCl) | 7.88(1H, dd, J=8Hz, 2Hz), 7.45(1H, dd, J=8Hz, 2Hz), 7.24(1H, t, J=8Hz), 7.01(1H, d, J=8Hz), 6.76(1H, s), 3.91–3.97(2H, m), 3.56–3.60(2H, m), 1.85–1.89(4H, m) (CDCl₃) | 330, 332 (FAB-MS) |
| 4 | [structure: benzoxazepinone with N-(CH₂)₄-Cl side chain, Cl on ring] oil | 2956, 1704 1644, 1604 1574, 1538 1479, 1236 (NaCl) | 7.86 7.89(1H, m), 7.43–7.47(1H, m), 7.22–7.26(1H, m), 7.02(1H, d, J=8Hz), 6.73(1H, s), 3.94(2H, t, J=6Hz), 3.57–3.60(2H, m), 1.86–1.89(4H, m) (CDCl₃) | 286 (FAB-MS) |
| Example | Chemical Structure | m.p. (Recrystallization Solvent) IR (cm$^{-1}$) | MS/Elementary NMR (δppm) | Analysis |

TABLE I-continued

| | Structure | IR | NMR / Mass |
|---|---|---|---|
| 5 | 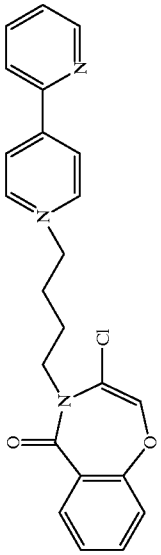 Cl⁻ | 3445 3008 1642 1603 1561 1475 1456 1342 1177 (KBr) | 9.21(2H, d, J=7Hz), 8.87(1H, d, J=4Hz), 8.81(2H, d, J=7Hz), 8.44(1H, d, J=8Hz), 8.11(1H, d, t, J=2Hz, 8Hz), 7.77(1H, dd, J=2Hz, 8Hz), 7.66(1H, dd, J=4Hz, 8Hz), 7.58(1H, dt, J=2Hz, 8Hz), 7.33(1H, t, J=8Hz), 7.14 (1H, d, J=8Hz), 7.10(1H, s), 4.71(2H, t, J=7Hz), 3.87 (2H, t, J=7Hz), 2.01–2.12(2H, m), 1.65–1.71(2H, m) (DMSO-d₆) |
| 6 | 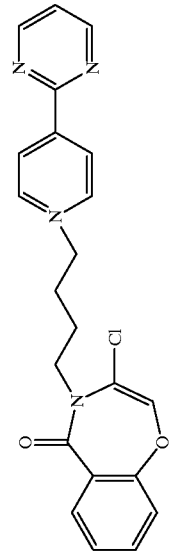 Cl⁻ | 3450 2365 1652 1553 1454 1414 1338 1201 1105 (KBr) | 9.49 (2H, d, J=7Hz), 8.96–8.98(4H, m), 7.82–7.84(1H, m), 7.45–7.47(2H, m), 7.23–7.28(1H, m), 7.02 (1H, d, J=7Hz), 6.74(1H, s), 5.19(2H, t, J=8Hz), 4.03(2H, t, J=7Hz), 2.20–2.25(2H, m), 1.93–1.98(2H, m) (CDCl₃) |
| 7 Step 1 | 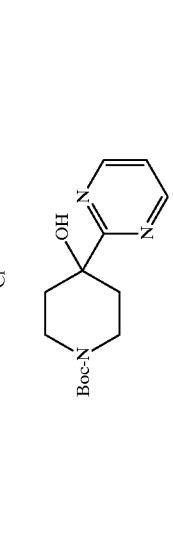 | 8.74(2H, d, J=5Hz), 7.22(1H, t, J=5Hz), 4.02–4.15(2H, m), 3.11–3.32(4H, m), 2.16–2.25(2H, m), 1.49 (9H, s) (CDCl₃) | FAB-Mass 280 (M+H)⁺ |
| 7 Step 2 | 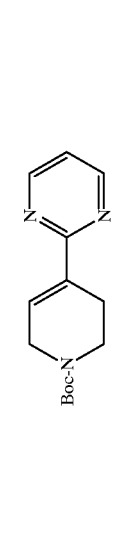 | 3018 1682 1556 1421 1368 1241 1168 (CHCl₃) | 8.69(2H, d, J=5Hz), 7.15–7.21(1H, m), 7.10(1H, t, J=5Hz), 4.17–4.22(2H, m), 3.64(2H, t, J=6Hz), 2.70–2.78(2H, m), 1.49(9H, s) (CDCl₃) FAB-MAS 262 (M+H)⁺ |
| 7 Step 3 | 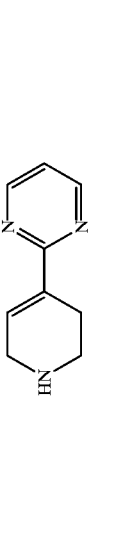 | 3021 2984 1571 1557 1423 1210 1206 (CHCl₃) | 8.68(2H, d, J=5Hz), 7.27–7.29(2H, m), 3.12(2H, t, J=6Hz), 2.62–2.66(2H, m), 7.09 (1H, t, J=5Hz), 3.62–3.64(2H, m), (CDCl₃) FAB-Mass 162 (M+H)⁺ |
| 8 Step 1 | 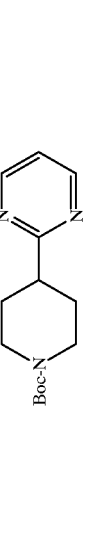 | 3024 1682 1563 1506 1426 1367 1248 (CHCl₃) | 8.68(2H, d, J=5Hz), 7.13(1H, t, J=5Hz), 4.15–4.28(2H, m), 3.00–3.06(1H, m), 2.85–2.91(2H, m), 1.98–2.02(2H, m), 1.75–1.87(2H, m), 1.47(9H, s) (CDCl₃) FAB-Mass 264 (M+H)⁺ |

TABLE I-continued
| | Structure | IR | NMR | FAB-Mass |
|---|---|---|---|---|
| 8 Step 2 | 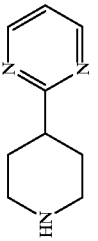 | 3023 3017 1574 1563 1427 1228 1206 (CHCl₃) | 8.68(2H, d, J=5Hz), 7.12(1H, t, J=5Hz), 3.20–3.24(2H, m), 2.99–3.06(1H, m), 2.75–2.82(2H, m), 2.00–2.04(2H, m), 1.76–1.86(2H, m) (CDCl₃) | 164 (M+H)⁺ |
| 9 Step 1 | 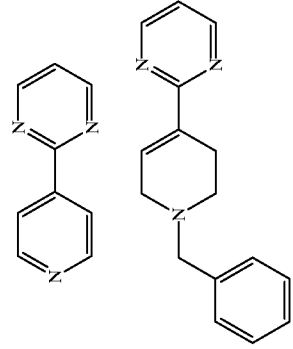 | 3027 1734 1668 1596 1547 1385 1218 (KBr) | 8.87 (2H, d, J=5Hz), 8.78(2H, d, J=5Hz), 8.29 (2H, d, J=5Hz), 7.30(1H, t, J=5Hz) (CDCl₃) | |
| 9 Step 2 | 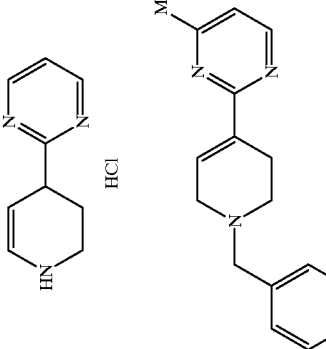 | 2910 2809 1654 1568 1533 1494 1424 1374 (KBr) | 8.67(2H, d, J=5Hz), 7.38–7.39(2H, m), 7.33(2H, t, J=7Hz), 7.26–7.27(1H, m), 7.20–7.22(1H, m), 7.07(1H, t, J=5Hz), 3.67(2H, s), 3.23–3.27(2H, m), 2.82–2.88(4H, m) (CDCl₃) | |
| 9 Step 3 | | 3374 2956 2793 2612 1659 1608 1568 1556 1426 1390 (KBr) | 9.27(2H, brs), 8.81(2H, d, J=5Hz), 7.39(1H, t, J=5Hz), 7.15–7.18(1H, m), 3.81–3.87(2H, m), 3.30–3.36(2H, m), 2.81–2.85(2H, m) (DMSO-d₆) | |
| 10 Step 1 | 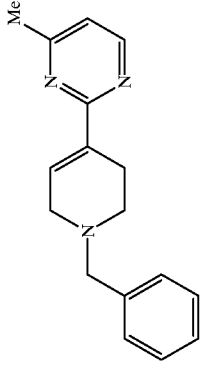 | 3019 2400 1652 1520 1418 1213 1046 (CHCl₃) | 8.50(1H, d, J=5Hz), 7.33–7.38(2H, m), 7.30–7.32(2H, m), 7.23–7.27(1H, m), 7.17(1H, d, J=3Hz), 6.92(1H, d, J=5Hz), 3.66 (2H, s), 3.25(2H, d, J=3Hz), 2.74(4H, s), 2.48(3H, s) (CDCl₃) | |
| 10 Step 2 | 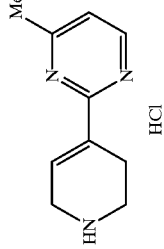 | 2956 2841 1657 1578 1554 1441 1393 1367 1251 (KBr) | 9.08–9.35(2H, brs), 8.65(1H, d, J=5Hz), 7.28(1H, t, J=5Hz), 7.13(1H, s), 3.83(2H, brs), 3.30–3.31(2H, m), 2.79–2.80(2H, m), 2.47(3H, s) (DMSO-d₆) | |

TABLE I-continued

| | Structure | mp / IR | NMR | MS |
|---|---|---|---|---|
| 11 Step 1 | [piperidine-Boc with 2-pyridyl, H] | 3022 1683 1574 1420 1394 1367 1276 (CHCl₃) | 8.74(2H, d, J=5Hz), 7.23(1H, t, J=5Hz), 4.07–4.10(1H, m), 3.81–3.92(1H, m), 3.35–3.45(1H, m), 2.94–3.00(1H, m), 1.81–1.84(1H, m), 1.70–1.73(1H, m), 2.18–2.22(1H, m), 2.00–2.05(1H, m), 1.45(9H, s) (CDCl₃) | FAB-Mass 280 (M+H)⁺ |
| 11 Step 2 | [tetrahydropyridine-Boc with 2-pyridyl] | 1684 1570 1556 1421 1367 1280 (CHCl₃) | 8.67(2H, d, J=5Hz), 7.37–7.39(1H, m), 7.10(1H, t, J=5Hz), 4.44–4.48(2H, m), 3.58(2H, t, J=6Hz), 2.39–2.43(2H, m), 1.50(9H, s) (CDCl₃) | FAB-Mass 262 (M+H)⁺ |
| 11 Step 3 | [tetrahydropyridine-NH with 2-pyridyl] | 3036 2952 1653 1627 1569 1558 1424 1229 (CHCl₃) | 8.66(2H, d, J=5Hz), 7.36–7.38(1H, m), 7.09(1H, t, J=5Hz), 3.95(2H, s), 3.08(2H, t, J=6Hz), 2.41–2.44(2H, m) (CDCl₃) | FAB-Mass 162 (M+H)⁺ |
| 12 Step 1 | [piperidine-Boc with 3-pyridyl] | 2848 1734 1681 1573 1422 1368 1269 (CHCl₃) | 8.67(2H, d, J=5Hz), 7.14(1H, t, J=5Hz), 4.28–4.35(1H, m), 4.10–4.18(1H, m), 2.98–3.16(2H, m), 2.75–2.85(1H, m), 2.14–2.20(1H, m), 1.75–1.84(2H, m), 1.55–1.60(1H, m), 1.46(9H, s) (CDCl₃) | FAB-Mass 264 (M+H)⁺ |
| 12 Step 2 | [piperidine-NH with 3-pyridyl] | 2929 2253 1466 1148 (CHCl₃) | 8.68 (2H, d, J=5Hz), 7.14 (1H, t, J=5Hz), 3.00–3.14(2H, m), 2.74–2.81(1H, m), 2.33–2.35(2H, m), 2.16–2.21(1H, m), 2.05–2.09(1H, m), 1.54–1.59(2H, m) (CDCl₃) | FAB-Mass 164 (M+H)⁺ |
| 13 | [benzoxazepinone-propyl-piperazine-2-pyridyl, Cl] | 178–180° C. (2) (EtOH–Et₂O) | 3698 2934 2572 2458 1662 1605 1586 1478 1456 1362 1201 (2) (KBr) | 10.1(1H, brs), 8.44 (2H, d, J=5Hz), 7.78–7.81(1H, m), 7.61(1H, t, J=7Hz), 7.33–7.37(1H, m), 7.18 (1H, s), 7.16(1H, d, J=7Hz), 6.76(1H, t, J=5Hz), 4.69–4.73(2H, m), 3.85–3.89(2H, m), 3.05–3.60(8H, m), 2.11–2.20(2H, m), (2) (DMSO-d₆) | MAB-Mass 400 (M+H)⁺ |

TABLE I-continued

| | | | | |
|---|---|---|---|---|
| 14 | [structure: chlorobenzoxazepinone-butyl-piperazine-phenylpyridine] | 158–161° C. (1) (EtOH–iPr₂O) | 3430 2949 1704 1657 1594 1480 1455 1438 1247 1158 984 (1) (KBr) | 8.08–8.11(1H, m), 7.77–7.81(1H, m), 7.48–7.63(2H, m), 7.33(1H, t, J=7Hz), 7.17(1H, d, J=7Hz), 7.16(1H, s), 6.80(1H, d, J=9Hz), 6.61 (4H, s), 6.60–6.65(1H, m), 3.85(2H, t, J=7Hz), 3.47(4H, t, J=5Hz), 2.44–2.50(4H, m), 2.40 (2H, t, J=7Hz), 1.62–1.72(2H, m), 1.48–1.58(2H, m) (1) (DMSO-d₆) Elementary Analysis C₂₆H₂₉N₄O₆Cl   C   H   N Calcd: 59.03 5.53 10.59 Found: 58.70 5.54 10.50 |
| 15 | [structure: chlorobenzoxazepinone-butyl-piperazine-isoquinoline] | 219–222° C. (2) (acetone) | 2448 1654 1608 1570 1546 1474 1450 1353 1100 (2) (KBr) | 11.33(1H, br, s), 8.92(1H, s), 8.21(1H, d, J=8Hz), 8.04(1H, t, J=8Hz), 7.96(1H, d, J=8Hz), 7.78–7.80(1H, m), 7.73(1H, t, J=8Hz), 7.58–7.62(1H, m), 7.34(1H, t, J=7Hz), 7.16(2H, t, J=7Hz), 4.74(2H, d, J=11Hz), 3.99(2H, br, s), 3.86(2H, t, J=7Hz), 3.64(2H, d, J=11Hz), 3.17–3.28(4H, m), 1.70–1.81(4H, m) (2) (DMSO-d₆) FAB-Mass 464(M+H)⁺ |

1 As fumarate, indicated as (1).
2 As chloride, indicated as (2).

| | | | | |
|---|---|---|---|---|
| 16 | [structure: 7-chloro-benzoxazepinone-butyl-piperazine-phenylpyridine] | 133–135° C. (3) (MeOH–CHCl₃–Et₂O) | 3450 2872 1664 1621 1568 1414 1300 1095 986 (3) (KBr) | 8.17(1H, d, J=9Hz), 7.82(1H, d, J=9Hz), 7.46(1H, t, J=9Hz), 7.22(1H, d, J=8Hz), 7.05(1H, s), 6.69(1H, s), 6.58–6.64(2H, m), 3.92(2H, t, J=7Hz), 3.54(4H, J=5Hz), 2.54(4H, t, J=5Hz), 2.43(2H, t, J=7Hz), 1.70–1.79(2H, m), 1.55–1.64(2H, m) (CDCl₃) FAB-Mass 447(M+H)⁺ |
| 17 | [structure: 7-methyl-benzoxazepinone-butyl-piperazine-pyridine] | 100–101° C. (3) (Et₂O) | 3434 2918 2593 1700 1622 1586 1552 1490 227 954 (3) (KBr) | 8.29(2H, d, J=5Hz), 7.66(1H, s), 7.23(1H, d, J=8Hz), 6.89(1H, d, J=8Hz), 6.70(1H, s), 6.46(1H, t, J=5Hz), 3.92(2H, t, J=7Hz), 3.82(4H, t, J=5Hz), 2.49(4H, t, J=5Hz), 2.42(2H, t, J=7Hz), 2.33(3H, s), 1.72–1.81(2H, m), 1.55–1.69(2H, m) (CDCl₃) FAB-Mass 428(M+H)⁺ |
| 18 | [structure: chloro-benzoxazepinone-butyl-tetrahydropyridine-pyridine] | 147–151° C. (2) (MeOH-acetone) | 3394 2930 1661 1605 1453 1422 1379 1200 (2) (KBr) | 10.15(1H, brs), 8.82(2H, d, J=5Hz), 7.79(1H, d, J=8Hz), 7.60(1H, t, J=8Hz), 7.33–7.43(2H, m), 7.13–7.14(3H, m), 4.09–4.13(1H, m), 3.85–3.88(3H, m), 3.65–3.70(1H, m), 3.24–3.27(3H, m), 2.85–2.99(2H, m), 1.10–1.85(4H, m) (2) (DMSO-d₆) FAB-Mass 411(M+H)⁺ |

TABLE I-continued

| | Structure | mp / form | IR | NMR / MS |
|---|---|---|---|---|
| 19 | (pyridin-2-yl piperidine, butyl, 3-chloro benzoxazepinone) | 110–113° C. (2) (acetone) | 3051 2946 1646 1604 1564 1478 1456 1426 (2) (KBr) | 10.15(1H, brs), 8.78(2H, d, J=5Hz), 7.80(1H, d, J=8Hz), 7.58–7.62(1H, m), 7.33–7.40(2H, m), 7.14–7.17(2H, m), 3.84–3.87(2H, m), 3.54–3.57(2H, m), 3.03–3.15(5H, m), 2.05–2.20(4H, m), 1.66–1.85(4H, m) (2) (DMSO-d$_6$) FAB-Mass 413(M+H)$^+$ |
| | 1 As chloride, indicated as (2). 2 As dichloride, indicated as (3). | | | |
| 20 | (pyridin-2-yl tetrahydropyridine, butyl, 3-chloro benzoxazepinone) | 124–126° C. (1) (acetone) | 2926 2576 1699 1649 1560 1478 1422 1378 (1) (KBr) | 8.73(2H, d, J=5Hz), 7.78(1H, d, J=8Hz), 7.58(1H, t, J=7Hz), 7.29–7.34(2H, m), 7.23(1H, s), 7.11–7.15(2H, m), 6.60(4H, s), 3.84–3.89(2H, m), 3.42–3.51(2H, m), 2.59–2.62(4H, m), 2.31–2.40(2H, m), 1.61–1.70(4H, m) (1)(DMSO-d$_6$) FAB-Mass 411(M+H)$^+$ |
| 21 | (pyridin-2-yl tetrahydropyridine, butyl, 3,7-dichloro benzoxazepinone) | 181–183° C. (1) (MeOH—Et$_2$O) | 3014 2539 1716 1658 1598 1556 1416 1298 (1) (KBr) | 8.67(2H, d, J=5Hz), 7.82(1H, d, J=7Hz), 7.26–7.27(1H, m), 7.22(1H, dd, J=2Hz, 7Hz), 7.05(1H, d, J=2Hz), 7.01(1H, t, J=5Hz), 6.70(1H, s), 3.92(2H, t, J=7Hz), 3.25–3.29(2H, m), 2.69–2.80(4H, m), 2.55(2H, t, J=7Hz), 1.66–1.75 (4H, m) (CDCl$_3$) FAB-Mass 445(M+H)$^+$ |
| 22 | (pyridin-2-yl piperidine, butyl, 3,7-dichloro benzoxazepinone) | amorphous (1) | 2926 1661 1619 1562 1429 (1) (KBr) | 8.74(2H, d, J=5Hz), 7.80(1H, d, J=9Hz), 7.41(1H, d, J=9Hz),7.33(1H, t, J=5Hz), 7.29(1H, s), 7.11(1H,s), 6.59(4H, s), 3.82–3.89(2H, m), 3.15–3.21(2H, m), 2.91–2.99(1H, m), 2.67–2.72(2H, m), 2.50–2.59(2H, m), 1.90–2.08(4H, m), 1.61–1.72(4H, m) (1) (DMSO-d$_6$) FAB-Mass 447(M+H)$^+$ |
| 23 | (pyridin-2-yl tetrahydropyridine, butyl, 3-chloro-7-methoxy benzoxazepinone) | 110–112° C. (1) (Et$_2$O) | 292 1657 1647 1616 1560 1540 1422 1328 (1) (KBr) | 8.76(2H, d, J=5Hz), 7.72(1H, d, J=9Hz), 7.32(1H, t, J=5Hz), 7.14–7.16(1H, m), 7.07(1H, s), 6.89(1H, d, J=2Hz), 6.69(1H, d, J=2Hz), 6.62(4H, s), 3.81–3.83(5H, m), 3.33–3.37(2H, m), 2.78–2.85(2H, m), 2.63–2.67(4H, m), 1.60–1.68(4H, m) (1) (DMSO-d$_6$) FAB-Mass 441(M+H)$^+$ |

TABLE I-continued

| | | | | |
|---|---|---|---|---|
| 24 | ![structure: MeO-benzoxazepinone-N-(CH2)4-piperidine-pyridine] | 178–181° C. (1) (acetone-Et$_2$O) | 2926 1665 2926 1665 1609 1561 1428 1264 (1) (KBr) | 8.76(2H, d, J=3Hz), 7.73(1H, d, J=9Hz), 7.38(1H, t, J=3Hz), 7.09(1H, d, J=4Hz), 6.90–6.92(1H, m), 6.70(1H, s), 6.63(4H, s), 3.80–3.85(5H, m), 3.52–3.57(2H, m), 3.05–3.18(5H, m), 2.16–2.20(2H, m), 1.95–2.05(2H, m), 1.63–1.72(4H, m), (1) (DMSO-d$_6$) | FAB-Mass 443(M+H)$^+$ |
| 25 | ![structure: Cl-benzoxazepinone-N-(CH2)4-piperidine-pyridine] | 167–170° C. (1) (MeOH–Et$_2$O) | 3432 2946 1660 1600 1567 1470 1414 1331 1201 (1) (KBr) | 8.51(1H, d, J=4Hz), 7.80(1H, d, J=8Hz), 7.73(1H, t, J=8Hz), 7.51(1H, d, J=8Hz), 7.40(1H, d, J=9Hz), 7.30(1H, s), 7.21(1H, t, J=6Hz), 7.12(1H, s), 6.65(1H, s), 6.62(4H, s), 3.85(2H, t, J=7Hz), 3.19–3.25(2H, m), 2.70–2.77(2H, m), 2.52–2.63(4H, m), 1.64–1.73(2H, m), 1.53–1.64(2H, m) (1) (DMSO-d$_6$) | FAB-Mass 444(M+H)$^+$ |
| 26 | ![structure: Cl-benzoxazepinone-N-(CH2)4-piperidine-pyridine] | 161–164° C. (1) (MeOH–Et$_2$O) | 3427 2947 1662 1599 1469 1475 1436 1289 1243 (1) (KBr) | 8.48(1H, d, J=4Hz), 7.80(1H, d, J=8Hz), 7.69(1H, t, J=4Hz), 7.41(1H, dd, J=2Hz, 8Hz), 7.30(1H, d, J=2Hz), 7.25(1H, d, J=8Hz), 7.18(1H, t, J=4Hz), 7.13(1H, s), 6.59(4H, s), 3.85(2H, t, J=7Hz), 3.06(2H, d, J=10Hz), 2.68–2.72(1H, m), 2.45–2.55(2H, m), 2.14–2.25(2H, m), 1.76–1.86(4H, m), 1.62–1.68(2H, m), 1.53–1.61(2H, m) (1) (DMSO-d$_6$) | FAB-Mass 446(M+H)$^+$ |
| 27 | ![structure: benzoxazepinone-N-(CH2)4-tetrahydropyridine-pyridine] | 148–151° C. (1) (MeOH–Et$_2$O) | 3420 2920 1662 1604 1454 1372 1332 1278 (1) (KBr) | 8.51(1H, d, J=5Hz), 7.79(1H, d, J=8Hz), 7.73(1H, t, J=8Hz), 7.57(1H, t, J=8Hz), 7.50(1H, d, J=8Hz), 7.32(1H, t, J=8Hz), 7.21(1H, t, J=4Hz), 7.14(1H, d, J=8Hz), 7.09(1H, s), 6.67(1H, s), 6.62(4H, s), 3.88(2H, t, J=7Hz), 2.70(2H, t, J=6Hz), 2.51–2.59(6H, m), 1.87–1.93(2H, m) (1) (DMSO-d$_6$) | FAB-Mass 396(M+H)$^+$ |
| 28 | ![structure: benzoxazepinone-N-(CH2)4-piperidine-pyridine] | amorphous (1) | 3440 2947 2656 2351 1651 1455 1336 1201 (1) (KBr) | 8.48(1H, d, J=4Hz), 7.79(1H, d, J=7Hz), 7.69(1H, t, J=8Hz), 7.58(1H, t, J=7Hz), 7.33(1H, t, J=8Hz), 7.25(1H, d, J=8Hz), 7.14–7.20(2H, m), 7.10(1H, s), 6.61(4H, s), 3.87(2H, t, J=6Hz), 3.08(2H, d, J=11Hz), 2.67–2.70(1H, m), 2.23(2H, t, J=10Hz), 1.79–1.88(6H, m) (1) (DMSO-d$_6$) | FAB-Mass 398(M+H)$^+$ |

1 As fumarate, indicated as (1).

TABLE I-continued

| | | | | |
|---|---|---|---|---|
| 29 | ![structure: 2-pyridyl-tetrahydropyridine-butyl-chloro-benzoxazepinone] | 123–126° C. (1) (MeOH—Et₂O) | 3441 2942 1644 1604 1454 1377 1329 1247 (1) (KBr) | 8.51(1H, d, J=4Hz), 7.78(1H, d, J=8Hz), 7.73(1H, t, J=7Hz), 7.57(1H, t, J=7Hz), 7.49(1H, d, J=8Hz), 7.32(1H, t, J=8Hz), 7.22(1H, t, J=4Hz), 7.13(1H, d, J=8Hz), 7.11(1H, s), 6.64(1H, s), 6.60(4H, s), 3.83(2H, t, J=7Hz), 3.19–3.22(2H, m), 2.70(2H, t, J=6Hz), 2.59–2.63(2H, m), 2.49–2.58(2H, m), 1.64–1.75(2H, m), 1.55–1.63(2H, m), 1.35–1.45(2H, m) (1) (DMSO-d₆) | FAB-Mass 424(M+H)⁺ |
| 30 | ![structure: 6-methyl-2-pyridyl tetrahydropyridine variant] | 121–124° C. (1) | 3424 2940 2582 1655 1578 1454 1372 1330 1249 (1) (KBr) | 8.63(1H, d, J=5Hz), 7.78–7.80(1H, m), 7.58–7.62(1H, m), 7.34(1H, t, J=8Hz), 7.25(1H, d, J=5Hz), 7.15–7.17(1H, m), 7.09(1H, s),6.63(4H, s), 3.80–3.88(2H, m), 2.95–3.40(2H, m), 2.73–2.80(2H, m), 2.48–2.57(4H, m), 2.46(3H, s), 1.65–1.73 (4H, m) (1) (DMSO-d₆) | FAB-Mass 425(M+H)⁺ |
| 31 | ![structure: 2-pyridyl-piperidine variant] | 158–161° C. (2) (acetone) | 3428 2946 2672 1648 1540 1454 1378 1330 1241 (2) (KBr) | 9.71(1H, br), 8.55–8.59(1H, m), 7.89–7.91(1H, m), 7.79(1H, t, J=8Hz), 7.60(1H, t, J=8Hz), 7.31–7.40(3H, m), 7.14–7.18(2H, m), 3.84–3.87(2H, m), 3.55–3.58(2H, m), 2.95–3.18(5H, m), 2.04–2.15(4H, m), 1.68–1.89(4H, m) (2) (DMSO- d₆) | FAB-Mass 412(M+H)⁺ |

1 As fumarate, indicated as (1).
2 As chloride, indicated as (2).

TABLE I-continued
| | | | |
|---|---|---|---|
| 32 | 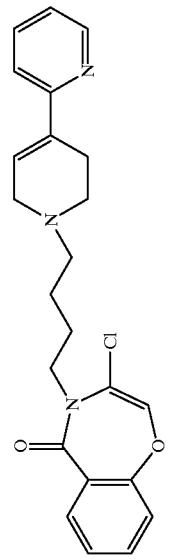 | 145–147° C. (2) (MeOH-acetone) 3416 2928 2695 1652 1604 1560 1455 1381 1340 1198 (2) (KBr) | 10.74(1H, br), 8.61–8.63(1H, m), 7.95–7.97(1H, m) 7.79(1H, dd, J=2, 8Hz), 7.70–7.72(1H, m) 7.60(1H, t, J=8Hz), 7.42–7.44(1H, m) 7.34(1H, t, J=8Hz), 7.14–7.17(2H, m), 6.74–6.76(1H, m), 4.03–4.08(1H, m), 3.84–3.87(3H, m), 3.64–3.67(1H, m), 3.21–3.25(3H, m), 2.91–2.93(2H, m), 1.84–1.86(2H, m), 1.70–1.76(2H, m), (2) (DMSO-d$_6$) | FAB-Mass 410(M+H)$^+$ |
| 33 | 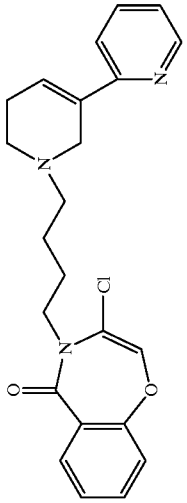 | amorphous (1) 3439 2933 1700 1683 1630 1570 1433 1291 (1) (KBr) | 8.50 (1H, d, J=5Hz) 7.79(1H, d, J=7Hz), 7.74(1H, t, J=7Hz), 7.58–7.62(2H, m), 7.33(1H, t, J=7Hz), 7.25(1H, t, J=5Hz), 7.12–7.15(2H, m), 6.72(1H, s), 6.60(4H, s), 3.90–3.94(2H, m), 3.64–3.68(2H, m), 2.73–2.80(4H, m), 2.39–2.40(2H, m), 1.66–1.71(4H, m) (1) (DMSO-d$_6$) | FAB-Mass 410(M+H)$^+$ |
1 As fumarate, indicated as (1).
2 As chloride, indicated as (2).

INDUSTRIAL APPLICABILITY

As explained above, according to the present invention, it is possible to industrially advantageously produce a 4-substituted-3-halogeno-1,4-benzoxazepine derivative, an important compound which may be used as a pharmaceutical for psychoneurotic disorders such as anxiety neurosis, phobias, obsessive-compulsive disorders, schizophrenia, post-cardiac trauma stress disorders, depression disorders, psychosomatic disorders, disorders such as eating disorders, menopausal disorders, infantile autism and also emesis or disorders involving the cerebral circulatory system accompanying cerebral infarction and cerebral hemorrhaging or as a synthesizing starting material or intermediate of pharmaceuticals etc., without the risk of occurrence of hydrochloric acid gas or a sudden rise in temperature or bumping in a neutralization reaction for treatment or decomposition of excessive acid chloride as in the process of the conventional method and further at a high yield without the accompanying difficulty of separation of the starting compound and the desired compound.

What is claimed is:

1. A process for producing 4-substituted-3-halogeno-1,4-benzoxazepin derivative or the salt thereof comprising:

deprotonizing a benzoxazepine derivative having the formula (II):

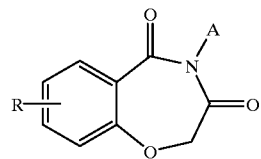

(II)

wherein R indicates a hydrogen atom, halogen atom, $C_1$ to $C_4$ lower alkyl group, $C_1$ to $C_4$ lower alkoxy group, or hydroxy group, and A indicates a $C_2$ to $C_5$ halogenoalkyl group or a group having the formula (III):

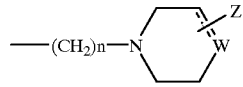

(III)

wherein n is an integer of 2 to 5, the dotted line indicates the presence or absence of a bond, W indicates a carbon atom, methine, methylene, or nitrogen atom, where when W is a nitrogen atom, Z bonds with W and the dotted line indicates the absence of a bond, and Z indicates an aromatic hydrocarbon group which may be substituted or a heterocyclic group which may be substituted, with a base; and then, reacting the deprotonized product with a phosphate halide to produce an intermediate having the formula (IV):

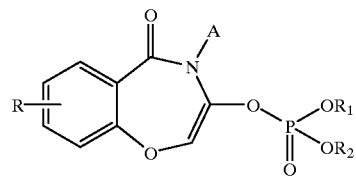

(IV)

wherein, R and A are as defined above, and $R_1$ and $R_2$ independently indicate, a $C_1$ to $C_2$ lower alkyl group or phenyl group or $R_1$ and $R_2$ together indicate an ethylene group (—$CH_2CH_2$—); and then, reacting the resultant intermediate (IV) with a reagent selected from (i) a complex of a tri($C_1$ to $C_4$) alkylphosphine, triarylphosphine, or phenyldi($C_1$ to $C_4$) alkylphosphine with chlorine or bromine, (ii) a tri($C_1$ to $C_4$) alkylphosphine, triarylphosphine, or phenyldi($C_1$ to $C_4$) alkylphosphine and a chlorine gas or liquid bromine, (iii) a tri($C_1$ to $C_4$) alkylphosphine, triarylphosphine, or phenyldi($C_1$ to $C_4$) alkylphosphine and tetrachloromethane or tetrabromomethane, or (iv) a halogenated phosphite ester to produce a 4-substituted-3-halogeno-1,4-benzoxazepine derivative having the formula (I)

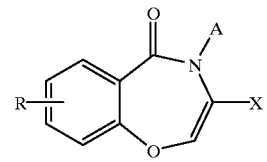

(I)

wherein, R and A are as defined above and X indicates a chlorine atom or a bromine atom, or its salt.

2. A process as claimed in claim 1, wherein R in the formulae (I), (II) and (IV) indicates a hydrogen atom or halogen atom, X indicates a chlorine atom, A indicates a $C_2$–$C_5$ halogenoalkyl group or a group having the formula (XXVI) or (XXVII):

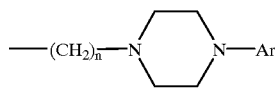

(XXVI)

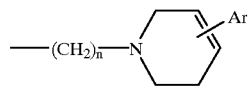

(XXVII)

wherein n is an integer of 2 to 5, Ar is a phenyl group, 2-pyridyl group or 2-pyrimidinyl group.

3. A process as claimed in claim 1, wherein the compound having the formula (II) is reacted with 1 to 1.2 equivalents of the base at a temperature of −78° C. to 0° C. in the presence of an organic solvent.

4. A process as claimed in claim 1, wherein the amount of the phosphate halide is 1 to 1.2 equivalents based upon the compound having the formula (II).

5. A process as claimed in claim 1, wherein the intermediate having the formula (IV) is reacted with 1 to 2 equivalents, based upon the intermediate (IV), of the reagent (i), (ii), (iii), or (iv) at a room temperature to 80° C. in the presence of an organic solvent.

* * * * *